United States Patent [19]

Hauel et al.

[11] Patent Number: 4,696,931
[45] Date of Patent: Sep. 29, 1987

[54] IMIDAZOLE DERIVATIVES AND PHARMACEUTICAL COMPOSITIONS CONTAINING THEM

[75] Inventors: Norbert Hauel; Volkhard Austel, both of Biberach; Joachim Heider, Warthausen; Manfred Reiffen; Willi Diederen, both of Biberach, all of Fed. Rep. of Germany

[73] Assignee: Dr. Karl Thomae GmbH, Biberach an der Riss, Fed. Rep. of Germany

[21] Appl. No.: 728,754

[22] Filed: Apr. 30, 1985

Related U.S. Application Data

[62] Division of Ser. No. 506,454, Jun. 21, 1983, Pat. No. 4,582,837.

[30] Foreign Application Priority Data

Jul. 1, 1982 [DE] Fed. Rep. of Germany ....... 3224512

[51] Int. Cl.$^4$ .................... C07D 473/00; A61K 31/52
[52] U.S. Cl. ..................................... 514/261; 544/277
[58] Field of Search ................ 544/264, 277; 514/261, 514/266

[56] References Cited

U.S. PATENT DOCUMENTS 3,985,891 10/1976 Kutter et al. .................. 546/118
4,299,834 11/1981 Austel et al. .................. 544/264 X
4,327,100 4/1982 Austel et al. .................. 546/118

FOREIGN PATENT DOCUMENTS 72926 3/1983 European Pat. Off. .
79083 5/1983 European Pat. Off. .
2305339 8/1974 Fed. Rep. of Germany .
2113675 8/1983 United Kingdom .

OTHER PUBLICATIONS

Chemical Abstracts, vol. 94, No. 25, Jun. 22, 1981, 208769f.
Burger, ed., *Medicinal Chemistry*, 3rd ed., Wiley-Interscience, (1970), pp. 74–76.

Primary Examiner—Donald G. Daus
Assistant Examiner—William A. Teoli, Jr.
Attorney, Agent, or Firm—Weissenberger, Hammond & Littell

[57] ABSTRACT

There are disclosed novel imidazole derivatives of the formula.

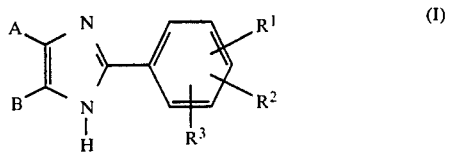

and derivatives of the formula

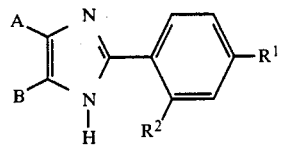

the tautomers thereof, and non-toxic, pharmacologically acceptable addition salts thereof with inorganic or organic acids. The compounds described herein are useful in treating cardiac insufficiency.

7 Claims, No Drawings

IMIDAZOLE DERIVATIVES AND PHARMACEUTICAL COMPOSITIONS CONTAINING THEM

This is a division of copending application Ser. No. 506,454, filed June 21, 1983, now U.S. Pat. No. 4,582,837.

Imidazole derivatives with valuable pharmacological properties have already been described in U.S. Pat. No. 3,985,891 and European Patent Application Nos. 24,290 and 22,495. It has now been found that novel imidazole derivatives of the formula

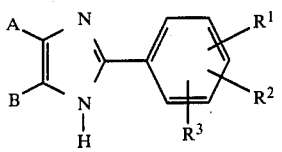

and the tautomers and acid addition salts thereof, more specifically, the non-toxic, pharmacologically acceptable acid addition salts thereof with inorganic or organic acids, which differ from known imidazole derivatives with regard to the $R^1$ substituent, have superior pharmacological properties, more particularly, an effect on the contractility of the myocardium.

In Formula I,

A and B, together with the two carbon atoms between them, represent a group of the formula

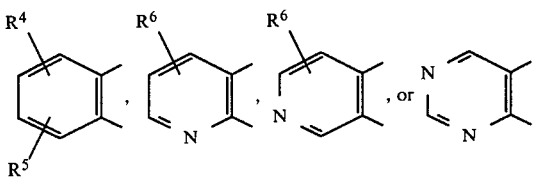

where $R^4$ is a hydrogen, halogen, alkyl, hydroxyl, alkoxy, trifluoromethyl, cyano, carboxyl, alkoxycarbonyl, aminocarbonyl, alkylaminocarbonyl, dialkylaminocarbonyl, hydroxyalkyl, nitro, amino, alkanoylamino, alkoxycarbonylamino, aminocarbonylamino, alkylaminocarbonylamino, dialkylaminocarbonylamino, alkanesulfonylamino, or N-alkyl-alkanesulfonylamino, $R^5$ is a hydrogen, halogen, alkyl, hydroxyl, or alkoxy, and $R^6$ is a hydrogen, halogen, or alkyl, the above-mentioned alkyl moieties each having from 1 to 3 carbon atoms;

$R^1$ is an alkanesulfonyloxy, trifluoromethanesulfonyloxy, alkanesulfonylamino, N-alkyl-alkanesulfonylamino, trifluoromethanesulfonylamino, N-alkyl-trifluoromethanesulfonylamino, alkylsulfenylmethyl, alkylsulfinylmethyl, or alkylsulfonylmethyl, or a carbonyl group substituted by a hydroxyl, alkoxy, amino, alkylamino, or dialkylamino, each alkyl moiety of the above-mentioned groups containing from 1 to 3 carbon atoms, or a sulfonyl substitued by an amino, alkylamino, dialkylamino, or cyclic amino, each alkyl moiety containing from 1 to 5 carbon atoms and each imino group containing from 4 to 7 carbon atoms, with the proviso that a methylene group in the 4-position of the cyclic imino may be replaced by a sulfur or oxygen atom or a nitro or cyano group;

$R^2$ is a hydrogen, alkyl, alkoxy, or dialkylamino, each alkyl moiety having from 1 to 3 carbon atoms; and $R^3$ is a hydrogen or alkoxy having from 1 to 3 carbon atoms.

The present invention thus relates to the novel benzimidazoles, imidazo[4,5-b]pyridines, imidazo[4,5-c]pyridines, and purines of Formula I above, and the tautomers and acid addition salts thereof, particularly the non-toxic, pharmacologically acceptable acid addition salts thereof with inorganic or organic acids. The invention also relates to processes for preparing them as well as to pharmaceutical compositions containing these compounds.

The definitions of the groups set forth above may include, for example, the following:

$R^1$ may represent a methanesulfonyloxy, ethanesulfonyloxy, n-propanesulfonyloxy, isopropanesulfonyloxy, trifluoromethanesulfonyloxy, methylsufenylmethyl, ethylsulfenylmethyl, n-propylsulfenylmethyl, methylsulfinylmethyl, ethylsulfinylmethyl, isopropylsulfinylmethyl, methylsulfonylmethyl, ethylsulfonylmethyl, n-propylsulfonylmethyl, methanesulfonylamino, ethanesulfonylamino, n-propanesulfonylamino, trifluoromethanesulfonylamino, N-methyl-methanesulfonylamino, N-ethyl-methanesulfonylamino, N-methyl-ethanesulfonylamino, N-ethyl-ethanesulfonylamino, N-isopropylethanesulfonylamino, N-methyl-n-propanesulfonylamino, N-n-propyl-n-propanesulfonylamino, N-methyl-trifluoromethanesulfonylamino, N-ethyl-trifluoro-methanesulfonylamino, N-isopropyl-trifluoromethanesulfonylamino, nitro, cyano, carboxyl, methoxycarbonyl, ethoxycarbonyl, propoxycarbonyl, isopropoxycarbonyl, aminocarbonyl, methylaminocarbonyl, ethylaminocarbonyl, dimethylaminocarbonyl, di-n-propylaminocarbonyl, N-methyl-ethylaminocarbonyl, pyrrolidinosulfonyl, piperidinosulfonyl, hexamethylene-iminosulfonyl, aminosulfonyl, methylaminosulfonyl, ethylaminosulfonyl, n-propylaminosulfonyl, n-butylaminosulfonyl, n-pentylaminosulfonyl, dimethylaminosulfonyl, diethylaminosulfonyl, di-n-propylaminosulfonyl, N-methylisopropylaminosulfonyl, or morpholinosulfonyl;

$R^2$ may represent a hydrogen, methyl, ethyl, propyl, isopropyl, methoxy, ethoxy, propoxy, dimethylamino, diethylamino, or N-methyl-n-propylamino;

$R^3$ may represent a hydrogen, methoxy, ethoxy, propoxy, or isopropoxy;

$R^4$ may represent a hydrogen, fluorine, chlorine, bromine, methyl, ethyl, propyl, isopropyl, hydroxyl, methoxy, ethoxy, propoxy, isopropoxy, cyano, carboxyl, methoxycarbonyl, ethoxycarbonyl, isopropoxycarbonyl, aminocarbonyl, methylamioncarbonyl, ethylaminocarbonyl, propylaminocarbonyl, dimethylaminocarbonyl, diethylaminocarbonyl, dipropylaminocarbonyl, methyl-ethylaminocarbonyl, methyl-isopropylaminocarbonyl, ethylpropylaminocarbonyl, hydroxymethyl, 1-hyroxyethyl, 2-hydroxyethyl, 1-hydroxypropyl, 2-hydroxypropyl, 3-hydroxypropyl, nitro, amino, formylamino, acetamino, propionylamino, methoxycarbonylamino, ethoxycarbonylamino, propoxycarbonylamino, isopropoxycarbonylamino, aminocarbonylamino, methylaminocarbonylamino, ethylaminocarbonylamino, propylaminocarbonylamino, dimethylaminocarbonylamino, diethylaminocarbonylamino, diisopropylaminocarbonylamino, methyl-ethylaminocarbonylamino, ethyl-propylaminocarbonylamino, methanesulfonylamino, ethanesulfonylamino, propanesulfonylamino, isopropanesulfonylamino, N-methyl-methanesulfonylamino, N-ethyl-methanesulfonylamino, N-propylmethanesulfonylamino, or N-ethyl-ethanesulfonylamino;

$R^5$ may represent a hydrogen, fluorine, chlorine, bromine, methyl, ethyl, propyl, isopropyl, hydroxyl, methoxy, ethoxy, propoxy, or isopropoxy; and $R^6$ may represent a hydrogen, fluorine, chlorine, bromine, methyl, ethyl, propyl, or isopropyl.

Preferred compounds of Formula I are those wherein

A and B together with the two carbon atoms between them represent a group of formula

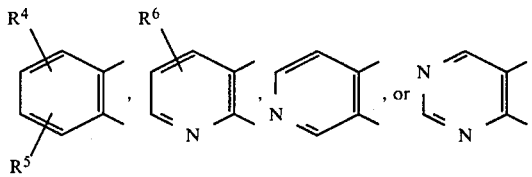

where $R^4$ represents a hydrogen, fluorine, chlorine, bromine, trifluoromethyl, cyano, methyl, hydroxyl, methoxy, hydroxymethyl, carboxyl, methoxycarbonyl, aminocarbonyl, methylaminocarbonyl, nitro, amino, acetylamino, methoxycarbonylamino, methanesulfonylamino, aminocarbonylamino, or methylaminocarbonylamino, $R^5$ represents a hydrogen, methyl, or methoxy, and $R^6$ represents a methyl, hydrogen, or chlorine, $R^1$ represents an alkanesulfonyloxy, trifluoromethanesulfonyloxy, alkylsulfenylmethyl, alkylsulfinylmethyl, alkylsulfonylmethyl, alkanesulfonylamino, N-alkyl-alkanesulfonylamino, trifluoromethanesulfonylamino, N-alkyl-trifluoromethanesulfonylamino, a carbonyl substituted by a hydroxyl, alkoxy, amino, alkylamino, or dialkylamino, or a sulfonyl substituted by an amino, dialkylamino, or morpholino, each of the alkyl moieties containing 1 to 2 carbon atoms, or a nitro, cyano, or alkylaminosulfonyl having from 1 to 4 carbon atoms;

$R^2$ represents a hydrogen, alkyl having from 1 to 3 carbon atoms, or alkoxy or dialkylamino having 1 or 2 carbon atoms in each alkyl moiety; and $R^3$ represents a hydrogen or methoxy, the tautomers thereof, and non-toxic, pharmacologically acceptable acid addition salts thereof with inorganic or organic acids.

However, particularly preferred are compounds of the formula

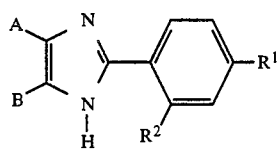

wherein

A and B together with the two carbon atoms between them represent a group of formula

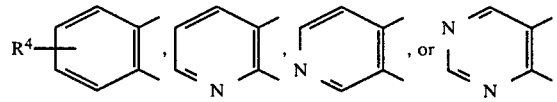

wherein $R^4$ represents a hydrogen, fluorine, methyl, hydroxyl, methoxycarbonyl, aminocarbonyl, amino, acetylamino, or cyano;

$R^1$ represents a methanesulfonyloxy, trifluoromethanesulfonyloxy, methanesulfonylamino, trifluoromethanesulfonylamino, methanesulfonylmethylamino, trifluoromethanesulfonylmethylamino, methylsulfenylmethyl, methylsulfinylmethyl, methylsulfonylmethyl, cyano, aminocarbonyl, aminosulfonyl, methylaminosulfonyl, or dimethylaminosulfonyl; and $R^2$ represents a hydrogen, methoxy, or dimethylamino.

Especially preferred are compounds of Formula Ia wherein

A and B together with the two carbon atoms between them represent a group of formula

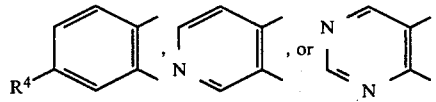

where $R^4$ represents a hydrogen, hydroxyl, cyano, aminocarbonyl, or acetylamino;

$R^1$ represents a methanesulfonyloxy, methansulfonylamino, N-methyl-methanesulfonylamino, or trifluoromethanesulfonyloxy; and $R^2$ represents a methoxy, the tautomers thereof, and non-toxic, pharmacologically acceptable acid addition salts thereof with inorganic or organic acids.

The compounds according to the invention may be prepared as follows:

Method A

A compound of the formula

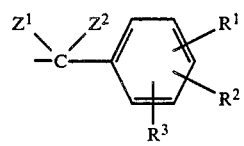 (II)

optionally prepared in the reaction mixture, wherein A and B are as defined above and one of X or Y represents a hydrogen and the other of X or Y represents, or both X and Y represent, a group of the formula

wherein $R^1$ to $R^3$ are as defined above; and $Z^1$ and $Z^2$, which may be the same or different, each represent an optionally substituted amino or a hydroxyl or mercapto which is optionally substituted by lower alkyl, or $Z^1$ and $Z^2$ together represent an oxygen or sulfur, an imino optionally substituted by an alkyl having from 1 to 3 carbon atoms, or an alkylenedioxy or alkylenedithio, each having 2 or 3 carbon atoms, is cyclized.

The cyclization is conveniently carried out in a solvent or mixture of solvents such as ethanol, isopropanol, glacial acetic acid, benzene, chlorobenzene, toluene, xylene, glycol, glycol monomethyl ether, diethylene glycol dimethyl ether, sulfolane, dimethylformamide, or tetraline or in an excess of the acylation agent used to prepare the compound of Formula II, for example, in the corresponding nitrile, anhydride, acid halide, ester, amide, or methoiodide, at temperatures of from about 0° to 250° C., but preferably at the boiling temperature of the reaction mixture, optionally in the presence of a condensation agent such as phosphorus oxychloride, thionyl chloride, sulfuryl chloride, sulfuric acid, p-toluenesulfonic acid, hydrochloric acid, phosphoric acid, polyphosphoric acid, or acetic anhydride or, optionally, also in the presence of a base such as potassium ethoxide or potassium tert.butoxide. However, cyclization may also be carried out without a solvent and/or condensation agent.

Method B

To prepare compounds of Formula I wherein $R^1$ represents an alkylsulfinylmethyl or alkylsulfonylmethyl, a compound of the formula

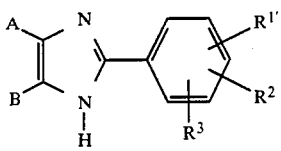

(III)

wherein A, B, $R^2$, and $R^3$ are as defined above and $R^{1'}$ represents an alkylsulfenylmethyl or alkylsulfinylmethyl, each having from 1 to 3 carbon atoms in the alkyl moiety, is oxidized. Oxidation is preferably carried out in a solvent or mixture of solvents, such as in water, water/pyridine, acetone, glacial acetic acid, dilute sulfuric acid, or trifluoroacetic acid, conveniently at temperatures of from about −80° to 100° C., dependent upon the oxidation agent used.

To prepare an alkylsulfinylmethyl compound of Formula I, the oxidation is conveniently carried out with one equivalent of the oxidation agent used, for example, with hydrogen peroxide in glacial acetic acid, trifluoroacetic acid, or formic acid at 0° to 20° C. or in acetone at 0° to 60° C., with a peracid such as performic acid in glacial acetic acid or trifluoroacetic acid at 0° to 50° C., with m-chloroperbenzoic acid in methylene chloride or chloroform at −20° to 60° C., with sodium metaperiodate in aqueous methanol or ethanol at −15° to 25° C., with bromine in glacial acetic acid or aqueous acetic acid, with N-bromosuccinimide in ethanol, with tert.butyl hypochlorite in methanol at −80° to −30° C., with iodobenzodichloride in aqueous pyridine at 0° to 50° C., with nitric acid in glacial acetic acid at 0° to 20° C., with chromic acid in glacial acetic acid or in acetone at 0° to 20° C., or with sulfuryl chloride in methylene chloride at −70° C., where the thioether-chlorine complex thus obtained is conveniently hydrolyzed with aqueous ethanol.

With regard to preparation of an alkylsulfonylmethyl compound of Formula I, oxidation is conveniently effected with one equivalent or with two or more equivalents of the oxidation agent used, for example, with hydrogen peroxide in glacial acetic acid, trifluoroacetic acid, or formic acid at 20° to 100° C. or in acetone at 0° to 60° C., with a peracid such as performic acid or m-chloroperbenzoic acid in glacial acetic acid, trifluoroacetic acid, methylene chloride, or chloroform at temperatures of from about 0° to 60° C., with nitric acid in glacial acetic acid at 0° to 20° C., or with chromic acid or potassium permanganate in glacial acetic acid, water/sulfuric acid, or acetone at 0° to 20° C.

Method C

To prepare compounds of Formula I wherein $R^1$ represents an alkanesulfonyloxy, trifluoromethanesulfonyloxy, alkanesulfonylamino, N-alkyl-alkanesulfonylamino, trifluoromethanesulfonylamino, or N-alkyltrifluoromethanesulfonylamino and/or $R^4$ represents an alkanesulfonylamino or N-alkyl-alkanesulfonylamino, a compound of the formula

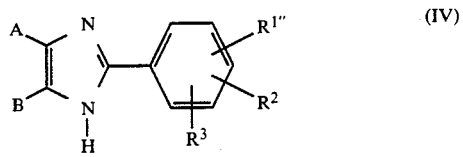

(IV)

wherein $R^2$, $R^3$, A and B are as defined above and $R^{1'''}$ represents a hydroxyl, amino, or N-alkylamino having from 1 to 3 carbon atoms in the alkyl moiety is reacted with a sulfonic acid of the formula $$R^7-CO_2OH \qquad (V)$$

wherein $R^7$ represents an alkyl having from 1 to 3 carbon atoms or a trifluoromethyl, in the presence of a dehydration agent and/or an agent which activates the acid or the amine or with the reactive derivatives thereof.

The reaction is conveniently effected in a solvent or mixture of solvents such as methylene chloride, ether, tetrahydrofuran, dioxane, or benzene, optionally in the presence of an acid-binding agent such as sodium carbonate, triethylamine, or pyridine, each of the last two optionally being used simultaneously as solvent, in the presence of an acid-activating or dehydrating agent such as thionyl chloride or phosphorus pentachloride, but preferably with a reactive derivative of a compound of Formula V, such as with the anhydride or halide thereof, for example, methanesulfonic acid chloride or ethanesulfonic acid chloride, preferably at temperatures of from about 0° to 100° C., such as at temperatures of from ambient temperature to about 50° C.

Method D

To prepare compounds of Formula I wherein $R^1$ represents a carbonyl or sulfonyl substituted by an amino, alkylamino, or dialkylamino and/or $R^4$ represents an aminocarbonyl, alkylaminocarbonyl, or dialkylaminocarbonyl, a compound of the formula

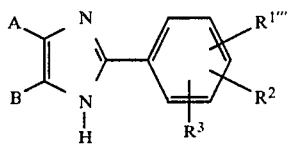 (VI)

wherein $R^2$, $R^3$, A, and B are as defined above and $R^{1'''}$ represents a carboxyl or hydroxysulfonyl, or a reactive derivative thereof, is reacted with an amine of the formula

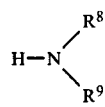 (VII)

wherein $R^8$ and $R^9$, which may be the same or different, each represent hydrogen or alkyl having from 1 to 5 carbon atoms, or with a reactive derivative thereof if $R^{1'''}$ represents a carboxyl or hydroxysulfonyl and/or $R^4$ represents a carboxyl.

The reaction is conveniently carried out in a solvent or mixture of solvents such as methylene chloride, chloroform, carbon tetrachloride, ether, tetrahydrofuran, dioxane, benzene, toluene, acetonitrile, or dimethylformamide, optionally in the presence of an acid-activating agent or a dehydrating agent, such as in the presence of ethyl chloroformate, thionyl chloride, phosphorus trichloride, phosphorus pentoxide,, N,N'-dicyclohexylcarbodiimide, N,N'-dicyclohexylcarbodiimide/N-hydroxysuccinimide, N,N'-carbonyldiimidazole, N,N'-thionyldiimidazole, or triphenylphosphine/carbon tetrachloride, or an agent which activates the amino group, such as phosphorus trichloride, and optionally in the presence of an inorganic base such as sodium carbonate or a tertiary organic base such as triethylamine or pyridine, which may simultaneously serve as solvent, at temperatures of from about −25° to 250° C., preferably from about −10° to the boiling temperature of the solvent used. Furthermore, any water formed during the reaction may be removed by azeotropic distillation, such as by heating with toluene in a water separator or by addition of a drying agent such as magnesium sulfate or a molecular sieve.

However, it is particularly advantageous to perform the reaction in a corresponding halide, such as a carboxylic or sulfonic acid chloride, and a corresponding amine, which may simultaneously serve as the solvent, at temperatures of from about 0° to 50° C.

If $R^4$ in a compound of Formula VI represents a carboxyl, this group is simultaneously converted into a corresponding aminocarbonyl, alkylaminocarbonyl, or dialkyaminocarbonyl group.

If a compound of Formula I is obtained wherein $R^1$ and/or $R^4$ represents a cyano, this may be converted by alcoholysis and/or hydrolysis into a corresponding compound wherein $R^1$ represents an alkoxycarbonyl with a total of from 2 to 5 carbon atoms, an aminocarbonyl, or a carboxyl group and/or $R^4$ represents an alkoxycarbonyl with a total of from 2 to 4 carbon atoms, an aminocarbonyl, or a carboxyl group, and/or a compound of Formula I wherein $R^1$ and/or $R^4$ represents a carboxyl may be converted by esterification into a corresponding compound of Formula I wherein $R^1$ represents an alkoxycarbonyl with a total of from 2 to 5 carbon atoms and/or $R^4$ represents an alkoxycarbonyl with a total of from 2 to 4 carbon atoms, and/or a compound of Formula I wherein $R^4$ represents an alkanoylamino may be converted by hydrolysis into a corresponding compound of Formula I wherein $R^4$ represents an amino, and/or a compound of Formula I wherein $R^4$ represents a nitro may be converted by reduction into a corresponding compound of Formula I wherein $R^4$ represents an amino, and/or a compound of Formula I wherein $R^4$ represents an amino may be converted, by converting it into a diazonium salt and subsequently heating it, into a corresponding compound of Formula I wherein $R^4$ represents a hydroxyl, and/or a compound of Formula I wherein $R^4$ represents an amino may be converted by carbamoylation into a corresponding compound of Formula I wherein $R^4$ represents an aminocarbonylamino or alkylaminocarbonylamino, and/or a compound of Formula I wherein $R^4$ represents an alkoxycarbonyl may be converted by amidation into a corresponding compound of Formula I wherein $R^4$ represents an aminocarbonyl, alkylaminocarbonyl, or dialkylaminocarbonyl, and/or a compound of Formula I wherein $R^4$ represents an alkoxycarbonyl may be converted by reduction into a corresponding compound of Formula I wherein $R^4$ represents a hydroxymethyl.

The subsequent alcoholysis and/or hydrolysis is conveniently effected either in the presence of an acid such as hydrochloric, sulfuric, phosphoric, or trichloroacetic acid or in the presence of a base such as sodium hydroxide or potassium hydroxide in a suitable solvent such as water, water/methanol, ethanol, water/ethanol, water/isopropanol, or water/dioxane at temperatures of from about −10° to 120° C., such as at temperatures of from ambient temperature to the boiling temperature of the reaction mixture.

The subsequent esterification is conveniently effected in a suitable solvent, such as in a corresponding alcohol, pyridine, toluene, methylene chloride, tetrahydrofuran, or dioxane in the presence of an acid-activating and/or dehydrating agent such as thionyl chloride, ethyl chloroformate, N,N'-carbonyliimidazole, or N,N'-dicyclohexylcarbodiimide or an isourea ether thereof, optionally in the presence of a reaction accelerator such as copper chloride, or by transesterification, such as with a corresponding carbonic acid diester, at temperatures of from about 0° to 100° C., preferably at temperature of from about 20° C. to the boiling temperature of the solvent in question.

The subsequent reduction of the nitro group is preferably carried out in a solvent such as water, water/ethanol, methanol, glacial acetic acid, ethyl acetate, or dimethylformamide, conveniently with hydrogen in the presence of a hydrogenation catalyst such as Raney nickel, platinum, or palladium/charcoal, with metals such as iron, tin, or zinc in the presence of an acid, with salts such as iron (II) sulfate, tin (II) chloride, sodium sulfide, sodium bisulfide, or sodium dithionite, or with hydrazine in the presence of Raney nickel at temperatures of from about 0° to 50° C., preferably at ambient temperature.

The subsequent heating of a diazonium salt, preferably the hydrochloride or hydrosulfate, is preferably carried out in an aqueous solvent such as water/ethanol, water/tetrahydrofuran, or water/dioxane at elevated temperature, such as at the boiling temperature of the solvent used. The diazonium salt required for this is conveniently prepared in a suitable solvent, for example, in water/hydrochloric acid, methanol/hydrochloric acid, ethanol/hydrochloric acid, or dioxane/hydrochloric acid, by diazotizing a corresponding compound with a nitrite, such as sodium nitrite or an ester of nitrous acid, at low temperatures, for example, at temperatures of from about −10° to 5° C.

The subsequent carbamoylation is carried out in an inert solvent such as water, methylene chloride, tetrahydrofuran, or dioxane with a corresponding isocyanate such as methyl isocyanate or potassium isocyanate in the presence of an acid such as acetic acid at temperatures of from about 0° to 50° C.

The subsequent amidation is carried out with a corresponding amine, possibly in a pressure vessel, conveniently in a solvent such as water, methylene chloride, chloroform, carbon tetrachloride, ether, tetrahydrofuran, dioxane, benzene, toluene, or dimethylformamide at temperatures of from about 50° to 150° C.

The subsequent reduction of the alkoxycarbonyl group is preferably effected with a metal hydride, for example, with a complex metal hydride such as lithium aluminium hydride, in a suitable solvent such as diethyl ether, tetrahydrofuran, or dioxane at temperatures of from about 0° to 100° C., preferably from about 20° to 60° C.

Moreover, the compounds of Formula I obtained may, if desired, subsequently be converted into the non-toxic, pharmacologically acceptable acid addition salts thereof with inorganic or organic acids. Examples of suitable acids include hydrochloric, hydrobromic, sulfuric, phosphoric, fumaric, succinic, tartaric, citric, lactic, maleic, and methanesulfonic acid.

The compounds of Formulae II to VII used as starting materials are known from the literature in some cases or may be obtained by methods known from the literature. For example, the compounds of Formula II may be obtained by acylation of corresponding 4,5-diamino compounds, and compounds of Formula III, IV, or VI may be obtained by subsequent condensation with a corresponding benzoic acid derivative and optional subsequent oxidation and/or acylation. (See, Belgium Patent No. 810,545 and European patent application No. 24,290.)

As mentioned above, the novel compounds of Formula I, the 1H tautomers thereof, and non-toxic, pharmacologically acceptable acid addition salts thereof have superior pharmacological properties, particularly a hypotensive and/or positive inotropic effect, and these effects are long-lasting. To demonstrate the properties of these compounds, the following compounds were tested for their biological properties in the manner described below:

A = 2-(2'-methoxy-4'-cyano-phenyl)-imidazo[4,5-b]pyridine,
B = 2-(2'-methoxy-4'-aminocarbonyl-phenyl)-imidazo[4,5-b]pyridine,
C = 8-(2'-methoxy-4'-cyano-phenyl)-purine,
D = 8-(2'-methoxy-4'-aminocarbonyl-phenyl)-purine,
E = 2-(2'-methoxy-4'-methylaminosulfonyl-phenyl)-imidazo[4,5-b]pyridine,
F = 8-(2'-methoxy-4'-methylaminosulfonyl-phenyl)-purine,
G = 2-(2'-methoxy-4'-methanesulfonyloxy-phenyl)-imidazo[4,5-b]pyridine,
H = 2-(2'-methoxy-4'-methanesulfonyloxy-phenyl)-benzimidazole,
I = 8-(2'-methoxy-4'-methanesulfonyloxy-phenyl)-purine,
K = 8-(2'-methoxy-4'-methanesulfonylamino-phenyl)-purine,
L = 2-(2'-methoxy-4'-N-methyl-methanesulfonylamino-phenyl)-imidazo[4,5-b]pyridine,
M = 8-(2'-methoxy-4'-N-methyl-methanesulfonylamino-phenyl)purine,
N = 2-(2'-methoxy-4'-methanesulfonylamino-phenyl)-benzimidazole,
O = 2-(2'-methoxy-4'-methylthiomethyl-phenyl)-imidazo[4,5-b]pyridine,
P = 5-cyano-2-(4'-methanesulfonyloxy-2'-methoxy-phenyl)-benzimidazole,
Q = 5-acetylamino-2-(4'-methanesulfonyloxy-2'-methoxy-phenyl)-benzimidazole,
R = 5-amino-2-(4'-methanesulfonylamino-2'-methoxy-phenyl)-benzimidazole,
S = 8-(2'-methoxy-4'-trifluoromethanesulfonyloxy-phenyl)purine,
T = 2-(4'-methanesulfonylamino-2'-methoxy-phenyl)-imidazo[4,5-c]pyridine,
U = 2-(4'-methanesulfonyloxy-2'-methoxy-phenyl)-imidazo[4,5-c]pyridine, and
V = 5-hydroxy-2-(4'-methanesulfonylamino-2'-methoxy-phenyl)-benzimidazole.

1. Determination of the effect on blood pressure and the positive inotropic activity in the anaesthetized cat:

The tests were carried out on cats which had been drugged with sodium pentobarbital (40 mg/kg i.p.). The animals breathed spontaneously. The arterial blood pressure was measured in the aorta abdominalis using a Statham pressure transducer (P 23 Dc). To determine the positive inotropic effect, the pressure in the left ventricle of the heart was measured using a catheter-tip monometer (Millar PC-350 A). From this, the contractility parameter $dp/dt_{max}$ was obtained by means of an analog differentiator. The substances to be tested were injected into a vena femoralis. The solvent used was physiological saline solution or Polydiol 200. Each substance was tested on at least three cats in a dosage of 2 mg/kg i.v.

The average values are set forth in the following table:

TABLE I

| Substance | Dosage (mg/kg i.v.) | Increase in $dp/dt_{max}$ (%) | Reduction in Blood Pressure (mm Hg) |
|---|---|---|---|
| A | 2.0 | +76 | −41/−50 |
| B | 2.0 | +99 | −9/−19 |
| C | 2.0 | +106 | −25/−34 |
| D | 2.0 | +103 | −20/−32 |
| E | 2.0 | +72 | −37/−33 |
| F | 2.0 | +124 | −57/−32 |
| G | 2.0 | +148 | −42/−40 |
| H | 2.0 | +94 | −24/−36 |
| I | 2.0 | +89 | −18/−50 |
| K | 2.0 | +79 | −27/−35 |
| L | 2.0 | +77 | −30/−42 |
| M | 2.0 | +69 | −37/−47 |
| N | 2.0 | +72 | −18/−30 |
| O | 2.0 | +73 | −24/−26 |
| P | 2.0 | +120 | −55/−55 |
| Q | 2.0 | +78 | −12/−32 |
| R | 2.0 | +107 | −30/−37 |
| S | 2.0 | +48 | −16/−32 |
| T | 2.0 | +112 | −22/−44 |
| U | 2.0 | +167 | −27/−27 |

TABLE I-continued

| Substance | Dosage (mg/kg i.v.) | Increase in dp/dt$_{max}$ (%) | Reduction in Blood Pressure (mm Hg) |
|---|---|---|---|
| V | 2.0 | +86 | −8/−28 |

2. Acute toxicity:

The acute toxicity of the test substances was determined as a guide on groups of ten mice after oral administration of a single dose of 300 mg/kg (observation period: 14 days):

TABLE II

| Substance | Approximate Acute Toxicity |
|---|---|
| G | >300 mg/kg (0 out of 10 animals died) |
| N | >300 mg/kg (0 out of 10 animals died) |

The new compounds are well tolerated. In the tests on Substances A to V, no toxic effects on the heart or circulatory damage were observed.

In view of their pharmacological properties the compounds of Formula I prepared according to the invention and the non-toxic, pharmacologically acceptable acid addition salts thereof are suitable for the treatment of cardiac insufficiency of various origins since they improve the contractile force of the heart and help the evacuation of the heart by lowering the blood pressure.

For such treatment, the compounds of Formula I or non-toxic, pharmacologically acceptable acid addition salts thereof can be processed, optionally in combination with other active ingredients, in manner known per se, together with one or more inert conventional carriers and/or diluents, such as corn starch, lactose, sucrose, microcrystalline cellulose, magnesium stearate, polyvinyl-pyrrolidone, citric acid, tartaric acid, water, water/ethanol, water/glycerine, water/sorbitol, water/polyethyleneglycol, propyleneglycol, cetyl stearyl alcohol, carboxymethylcellulose, or fatty substances such as hard fat, or suitable mixtures thereof, to form conventional galenic preparations such as tablets, coated tablets, capsules, powders, infusions, suspensions, solutions, or suppositories. A single dose for adults is from about 22.5 to 165 mg (from about 0.3 to 2.2 mg/kg of body weight), preferably from about 52.5 to 112.5 mg/kg (from about 0.7 to 1.5 mg/kg of body weight), administered from 1 to 4 times a day to achieve the desired results.

Dependent upon the type and body weight of the patient to be treated, on the type and severity of the disease, on the type of preparation and on the route of administration, which may be peroral, parenteral, or rectal, as well as on the period or interval over which the administration takes place, it may, however, be necessary to deviate from the above dosages. Thus it may be sufficient in some cases to administer more or less than the above-mentioned amounts of active ingredient. The optimum dosage and route of administration of the active ingredients which are necessary in each case can easily be determined by one skilled in the art.

The following examples are intended to illustrate the invention and should not be construed as limiting the invention thereto.

EXAMPLES

Preparation of Starting Materials

EXAMPLE A 2-(2'-Methoxy-4'-benzyloxy-phenyl)-benzimidazole

Amounts of 5.2 gm (20 mmol) of 2-methoxy-4-benzyloxybenzoic acid and 2.2 gm (20 mmol) of o-phenylenediamine were triturated together and mixed with 50 ml of phosphorus oxychloride, and the mixture was refluxed for 1.5 hours. After cooling, the solution was poured onto 300 gm of ice and made alkaline with 30% sodium hydroxide solution. The product precipitated was subjected to suction filtration, washed with water, and dried at 50° C. in a circulating air drier.

Yield: 3.5 gm (53% of theory),

R$_f$ value: 0.8 [silica gel; eluant: methylene chloride/ethanol (19:1)].

EXAMPLE B 2-(2'-Methoxy-4'-hydroxy-phenyl)-benzimidazole

A quantity of 3.3 gm (10 mmol) of 2-(2'-methoxy-4'-benzyloxy-phenyl)-benzimidazole was dissolved in 400 ml of ethanol and, after addition of 0.5 gm of palladium on charcoal (20%), treated with hydrogen (5 bar) in a Parr apparatus at 50° C. After all the hydrogen was taken up, the catalyst was removed by suction filtration, and the filtrate was concentrated by evaporation. The solid residue was triturated with ether, subjected to suction filtration, and dried.

Yield: 2.3 gm (95.8% of theory),

R$_f$ value: 0.36 [silica gel; eluant: methylene chloride/ethanol (19:1)].

EXAMPLE C 2-(2'-Methoxy-4'-chlorosulfonyl-phenyl)-imidazo[4,5-b]pyridine hydrochloride Five grams of 2-methoxy-4-chlorosulfonyl-benzoic acid (prepared from 4-amino-2-methoxy-benzoic acid via the corresponding diazonium compound) were dissolved in 400 ml of phosphorus oxychloride and heated to 80° C. for 30 minutes. Then, 3.6 mg of 2,3-diaminopyridine were added, and the mixture was refluxed for four hours. The reaction mixture was concentrated by evaporation in vacuo and re-evaporated with toluene, and the solid residue was processed further without any other purification.

EXAMPLE D 2-(2'-Methoxy-4'-chlorosulfonyl-phenyl)-purine hydrochloride

Prepared analogously to Example C from 2.5 gm of 2-methoxy-4-chlorosulfonyl benzoic acid and 2.4 gm of 4,5-diamino-pyrimidine (crystalline product obtained from dihydrochloride and 1 mol of common salt) by refluxing for eight hours. The solid crude product was processed further without any purification.

EXAMPLE E 2-(2'-Dimethylamino-4'-amino-phenyl)-imidazo[4,5-b]pyridine dihydrochloride An amount of 2.83 gm of 2-(2'-dimethylamino-4'-nitrophenyl)-imidazo[4,5-b]pyridine was hydrogenated in a mixture of 100 ml of methanol, 10 ml of concentrated methanolic hydrochloric acid, and 1 gm of palladium/charcoal for 4.5 hours at ambient temperature with hydrogen gas at 5 bar. The catalyst was then removed by filtration, the filtrate was concentrated by evaporation, and the residue was triturated with acetone to form crystals, filtered, and then washed with a mixture of ether and acetone.

Yield: 2.3 gm (70% of theory),
M.p.: 208°–210° C.

EXAMPLE F 2-(2'-Dimethylamino-4'-hydroxy-phenyl)-imidazo[4,5-b]pyridine dihydrochloride A quantity of 1.15 gm of 2-(2'-dimethylamino-4'-aminophenyl)-imidazo[4,5-b]pyridine was suspended in 25 ml of ice water, mixed with 2.5 ml of concentrated sulfuric acid, and cooled to −5° C. Then, a solution of 0.35 gm of sodium nitrite in 5 ml of water was slowly added dropwise, and the resulting mixture was stirred for 15 minutes at 0° C. The orange-yellow suspension formed was slowly added dropwise to a hot solution (90° C.) of 6 ml of concentrated sulfuric acid and 12 ml of water. Subsequently the mixture was evaporated down to a quarter of the volume and neutralized with aqueous ammonia. The precipitate formed was subjected to suction filtration and, after being dried, taken up in methanol, from which the dihydrochloride was precipitated with etheral hydrochloric acid.

Yield: 0.63 gm (42% of theory),
M.p.: 212°–214° C.

Preparation of Compounds According to the Invention

EXAMPLE 1

2-(2'-Methoxy-4'-methanesulfonyloxy-phenyl)-benzimidazole

An amount of 2.2 gm (9 mmol) of 2-(2'-methoxy-4'-hydroxy-phenyl)-benzimidazole was suspended in 40 ml of pyridine, and 2 ml of methanesulfonic acid chloride were added dropwise at ambient temperature under stirring. The mixture was heated to 50° C. for one hour and then mixed with 10 ml of water, and afterwards the solution was evaporated to dryness in vacuo. The solid residue was triturated with water, subjected to suction filtration, and recrystallized from ethanol.

Yield: 1.2 gm (41.9% of theory),
$R_f$ value: 0.67 [silica gel; eluant: methylene chloride/ethanol (19:1)].
M.p.: 197°–198° C.
$C_{15}H_{14}N_2O_4S$ (318.34)
Calculated: C, 56.59; H, 4.43; N, 8.80; S, 10.07. Found: C, 56.40; H, 4.43; N, 8.74; S, 10.20.

EXAMPLE 2

2-(2'-Methoxy-4'-methanesulfonyloxy-phenyl)-imidazo[4,5-b]pyridine

Prepared analogously to Example 1 from 2-(2'-methoxy-4'-hydroxyphenyl)-imidazo[4,5-b]pyridine and methanesulfonic acid chloride.

Yield: 67.3% of theory,
M.p.: 208°–209° C.
$C_{14}H_{13}N_3O_4S$ (319.3)
Calc.: C, 52.66; H, 4.10; N, 13.16; S, 10.04. Found: C, 52.41; H, 3.98; N, 13.22; S, 9.99.

EXAMPLE 3

2-(2',4'-Dimethoxy-3'-methanesulfonyloxy-phenyl)-imidazo[4,5-b]pyridine hydrochloride Prepared analogously to Example 1 from 2-(2',4'-dimethoxy-3'-hydroxy-phenyl)-imidazo[4,5-b]pyridine and methanesulfonic acid chloride.

Yield: 58.4% of theory,
M.p.: 202°–206° C. (decomposition).
$C_{15}H_{16}ClN_3O_5S$ (385.83)
Calc.: C, 46.69; H, 4.18; N, 10.89; Cl, 9.19. Found: C, 46.83; H, 4.13; N, 11.18; Cl, 9.47.

EXAMPLE 4

8-(2'-Methoxy-4'-methanesulfonyloxy-phenyl)-purine

Prepared analogously to Example 1 from 8-(2'-methoxy-4'-hydroxy-phenyl)-purine and methanesulfonic acid chloride.

Yield: 46.9% of theory,
M.p.: 225°–227° C.
$C_{13}H_{12}N_4O_4S$ (320.3)
Calc.: C, 48.75; H, 3.78; N, 17.49; S, 10.01. Found: C, 48.52; H, 3.72; N, 17.25; S, 10.00.

EXAMPLE 5

8-(2'-Methoxy-4'-ethanesulfonyloxy-phenyl)-purine

Prepared analogously to Example 1 from 8-(2'-methoxy-4'-hydroxy-phenyl)-purine and ethanesulfonic acid chloride.

Yield: 12% of theory,
M.p.: 195°–196° C.
$C_{14}H_{14}N_4O_4S$ (334.4)
Calc.: C, 50.29; H, 4.22; N, 16.76; S, 9.59. Found: C, 50.02; H, 4.15; N, 16.59; S, 9.83.

EXAMPLE 6

2-(2'-Methoxy-4'-ethanesulfonyloxy-phenyl)-imidazo[4,5-b]pyridine

Prepared analogously to Example 1 from 2-(2'-methoxy-4'-hydroxy-phenyl)-imidazo[4,5-b]pyridine and ethanesulfonic acid chloride.

Yield: 20.1% of theory,
M.p.: 206°–209° C.
$C_{15}H_{15}N_3O_4S$ (333.4)
Calc.: C, 54.04; H, 4.54; N, 12.60; S, 9.62. Found: C, 54.11; H, 4.59; N, 12.43; S, 9.71.

EXAMPLE 7

2-(2'-Methoxy-3'-methanesulfonyloxy-phenyl)-imidazo[4,5-b]pyridine

Prepared analogously to Example 1 from 2-(2'-methoxy-3'-hydroxy-phenyl)-imidazo[4,5-b]pyridine and methanesulfonic acid chloride.

Yield: 70.7% of theory,
M.p.: 153°–155° C.
$C_{14}H_{13}N_3O_4S$ (319.3)
Calc.: C, 52.66; H, 4.10; N, 13.16; S, 10.04. Found: C, 52.40; H, 3.96; N, 13.17; S, 10.04.

EXAMPLE 8

8-(2'-Methoxy-3'-methanesulfonyloxy-phenyl)-purine

Prepared analogously to Example 1 from 8-(2'-methoxy-3'-hydroxy-phenyl)-purine and methanesulfonic acid chloride.

Yield: 46.8% of theory,

M.p.: 187°–188° C.
C$_{13}$H$_{12}$N$_4$O$_4$S (320.3)
Calc.: C, 48.75; H, 3.78; N, 17.50; S, 10.01. Found: C, 48.70; H, 4.02; N, 17.37; S, 10.35.

EXAMPLE 9

2-(3'-Methoxy-5'-methanesulfonyloxy-phenyl)-imidazo[4,5-b]pyridine

Prepared analogously to Example 1 from 2-(3'-methoxy-5'-hydroxy-phenyl)-imidazo[4,5-b]pyridine and methanesulfonic acid chloride.
Yield: 15% of theory,
M.p.: 225°–227° C.
C$_{14}$H$_{13}$N$_3$O$_4$S (319.35)
Calc.: C, 52.65; H, 4.10; N, 13.15; S, 10.04. Found: C, 52.86; H, 4.32; N, 13.20; S, 9.91.

EXAMPLE 10

2-(3'-Methoxy-4'-methanesulfonyloxy-phenyl)-imidazo[4,5-b]pyridine

Prepared analogously to Example 1 from 2-(3'-methoxy-4'-hydroxy-phenyl)-imidazo[4,5-b]pyridine and methanesulfonic acid chloride.
Yield: 43.8% of theory,
M.p.: 235°–237° C.
C$_{14}$H$_{13}$N$_3$O$_4$S (319.3)
Calc.: C, 52.66; H, 4.10; N, 13.16; S, 10.04. Found: C, 52.80; H, 4.05; N, 13.11; S, 10.15.

EXAMPLE 11

5-Trifluoromethyl-2-(2'-methoxy-4'-methanesulfonyloxy-phenyl)-benzimidazole

Prepared analogously to Example 1 from 5-trifluoromethyl-2-(2'-methoxy-4'-hydroxy-phenyl)-benzimidazole and methanesulfonic acid chloride.
Yield: 50.8% of theory,
M.p.: 138°–140° C.
C$_{16}$H$_{13}$F$_3$N$_2$O$_4$S (386.36)
Calc.: C, 49.74; H, 3.39; N, 7.25; S, 8.30. Found: C, 49.43; H, 3.54; N, 7.17; S, 8.34.

EXAMPLE 12

5-Methoxy-2-(2'-methoxy-4'-methanesulfonyloxy-phenyl)-benzimidazole

Prepared analogously to Example 1 from 5-methoxy-2-(2'-methoxy-4'-hydroxy-phenyl)-benzimidazole and methanesulfonic acid chloride.
Yield: 88.2% of theory,
M.p.: 152°–154° C.
C$_{16}$H$_{16}$N$_2$O$_5$S (348.39)
Calc.: C, 55.16; H, 4.63; N, 8.04; S, 9.20. Found: C, 55.38; H, 4.78; N, 7.94; S, 9.28.

EXAMPLE 13

5-Cyano-2-(2'-methoxy-4'-methanesulfonyloxy-phenyl)-benzimidazole

Prepared analogously to Example 1 from 5-cyano-2-(2'-methoxy-4'-hydroxy-phenyl)-benzimidazole and methanesulfonic acid chloride.
Yield: 23.8% of theory,
M.p.: 225°–227° C.
C$_{16}$H$_{13}$N$_3$O$_4$S (343.37)
Calc.: C, 55.96; H, 3.82; N, 12.24; S, 9.34. Found: C, 55.71; H, 3.93; N, 12.08; S, 9.24.

EXAMPLE 14

2-(2'-Methoxy-4'-methanesulfonylamino-phenyl)-imidazo[4,5-c]pyridine

Quantities of 5.45 gm (50 mmol) of 3,4-diaminopyridine and 12.25 gm (50 mmol) of 2-methoxy-4-methanesulfonylaminobenzoic acid were triturated together and refluxed for four hours in 300 ml of phosphorus oxychloride. Excess phosphorus oxychloride was then distilled off, and the residue was mixed with 500 ml of water and adjusted to a pH of 8 with concentrated ammonia. The insoluble components were filtered off, the filtrate was saturated with sodium chloride, and the crude product precipitated. After purification by chromatography (800 gm of aluminum oxide: eluant: dichloromethane with 5 to 10% of ethanol), 4.8 gm (25.2% of theory) were obtained.
M.p.: >250° C.,
C$_{14}$H$_{14}$N$_4$O$_3$S (318.4)
Calc.: C, 52.81; H, 4.43; N, 17.60. Found: C, 52.61; H, 4.63; N, 17.35.
$^1$H-NMR spectrum (DMSO-d$_6$/CD$_3$OD): δ=3.2 (s, 3H); 4.1 (s, 3H); 6.9–7.3 (m, 2H); 7.5–7.8 (m, 1H); 8.2–8.5 (m, 2H); 8.9–9.0 (broad s, 1H) ppm.

The following compounds were prepared in analogous manner:

a. 2-(2'-Methoxy-4'-N-methyl-methanesulfonylaminophenyl)-imidazo[4,5-c]pyridine

Prepared from 3,4-diaminopyridine and 2-methoxy-4-N-methyl-methanesulfonylamino-benzoic acid.
Yield: 19.8% of theory,
M.p. >250° C.
C$_{15}$H$_{16}$N$_4$O$_3$S (332.4)
Calc.: C, 54.20; H, 4.85; N, 16.86. Found: C, 54.47; H, 4.91; N, 16.62.
$^1$H-NMR spectrum (DMSO-d$_6$/CD$_3$OD): δ=3.1 (s, 3H); 3.4 (s, 3H); 4.1 (s, 3H); 6.9–7.3 (m, 2H); 7.5–7.8 (m, 1H); 8.2–8.5 (m, 2H); 8.9–9.0 (broad s, 1H) ppm.

b. 2-(2'-Methoxy-4'-N-ethyl-methanesulfonylaminophenyl)-imidazo[4,5-c]pyridine

Prepared from 3,4-diaminopyridine and 2-methoxy-4-N-ethyl-methanesulfonyloxy-benzoic acid.
Yield: 16.9% of theory,
C$_{16}$H$_{18}$N$_4$O$_3$S (346.40)
Calc.: C, 55.47; H, 5.24; N, 16.18. Found: C, 55.58; H, 5.31; N, 15.92.
$^1$H-NMR spectrum (DMSO-d$_6$/CD$_3$OD): δ=1.0–1.3 (t, 3H); 3.1 (s, 3H); 3.6–4.0 (q, 2H); 4.1 (s, 3H); 6.9–7.3 (m, 2H); 7.5–7.8 (m, 1H); 8.2–8.5 (m, 2H); 8.9–9.0 (broad s, 1H) ppm.

EXAMPLE 15

2-(2'-Methoxy-4'-methanesulfonylamino-phenyl)-imidazo[4,5-b]pyridine

Prepared analogously to Example 14 from 2,3-diaminopyridine and 2-methoxy-4-methanesulfonylamino-benzoic acid.
Yield: 57.3% of theory,
M.p.: 236°–238° C.
R$_f$ value: 0.50 [silica gel; eluant: methylene chloride/ethanol (19:1)].

EXAMPLE 16

8-(2'-Methoxy-4'-methanesulfonylamino-phenyl)-purine

Prepared analogously to Example 14 from 4,5-diaminopyrimidine and 2-methoxy-4-methanesulfonylamino-benzoic acid.

Yield: 40.75% of theory,
M.p.: 237°–238° C.
$C_{13}H_{13}N_5O_3S$
Calc.: C, 48.89; H, 4.10; N, 21.93; S, 10.94. Found: C, 48.81; H, 4.37; N, 21.88; S, 9.95.

EXAMPLE 17

2-(2'-Methoxy-4'-N-methyl-methanesulfonylamino-phenyl)-imidazo[4,5-b]pyridine

Prepared analogously to Example 14 from 2,3-diaminopyridine and 2-methoxy-4-N-methyl-methanesulfonylamino-benzoic acid.

Yield: 57.2% of theory,
M.p.: 238°–240° C.
$C_{15}H_{16}N_4O_3S$ (332.4)
Calc.: C, 54.20; H, 4.85; N, 16.86; S, 9.65. Found: C, 54.20; H, 4.91; N, 16.68; S, 9.86.

EXAMPLE 18

8-(2'-Methoxy-4'-N-methyl-methanesulfonylamino-phenyl)purine

Prepared analogously to Example 14 from 4,5-diaminopyrimidine and 2-methoxy-4-N-methyl-methanesulfonylamino-benzoic acid.

Yield: 45.5% of theory,
M.p.: >250° C.
$C_{14}H_{15}N_5O_3S$ (333.4)
Calc.: C, 50.44; H, 4.54; N, 21.01; S, 9.62. Found: C, 50.15; H, 4.77; N, 20.77; S, 9.50.

EXAMPLE 19

2-(3'-Methoxy-4'-methanesulfonylamino-phenyl)-imidazo[4,5-b]pyridine

Prepared analogously to Example 14 from 2,3-diaminopyridine and 3-methoxy-4-methanesulfonylamino-benzoic acid.

Yield: 21.4% of theory,
M.p.: >250° C.
$C_{14}H_{14}N_4O_3S$ (318.4)
Calc.: C, 52.81; H, 4.43; N, 17.60; S, 10.07. Found: C, 52.60; H, 4.46; N, 17.94; S, 10.10.

EXAMPLE 20

8-(3'-Methoxy-4'-methanesulfonylamino-phenyl)-purine

Prepared analogously to Example 14 from 4,5-diaminopyrimidine and 3-methoxy-4-methanesulfonylamino-benzoic acid.

Yield: 11.2% of theory,
M.p.: >250° C.
$C_{13}H_{13}N_5O_3S$ (319.35)
Calc.: C, 48.89; H, 4.10; N, 21.93; S, 10.04. Found: C, 48.31; H, 4.45; N, 21.74; S, 10.80.

EXAMPLE 21

2-(3'-Methoxy-4'-N-methyl-methanesulfonylamino-phenyl)-imidazo[4,5-b]pyridine

Prepared analogously to Example 14 from 2,3-diaminopyridine and 3-methoxy-4-N-methyl-methanesulfonylaminobenzoic acid.

Yield: 38.8% of theory,
M.p.: >250° C.
$C_{15}H_{16}N_4O_3S$ (332.39)
Calc.: C, 54.20; H, 4.85; N, 16.85; S, 9.65. Found: C, 54.59; H, 5.22; N, 16.57; S, 9.55.

EXAMPLE 22

9-(3'-Methoxy-4'-N-methyl-methanesulfonylamino-phenyl)purine

Prepared analogously to Example 14 from 4,5-diaminopyridine and 3-methoxy-4-N-methyl-methanesulfonylaminobenzoic acid.

Yield: 9.6% of theory,
M.p.: >250° C.
$C_{14}H_{15}N_5O_3S$ (333.38)
Calc.: C, 50.44; H, 4.54; N, 21.00; S, 9.62. Found: C, 50.71; H, 5.10; N, 20.58; S, 9.59.

EXAMPLE 23

2-(2'-Methoxy-4'-methanesulfonylamino-phenyl)-benzimidazole

Prepared analogously to Example 14 from o-phenylenediamine and 2-methoxy-4-methanesulfonylamino-benzoic acid.

Yield: 23.6% of theory,
M.p.: >250° C.
$C_{15}H_{15}N_3O_3S$ (317.38)
Calc.: C, 56.76; H, 4.76; N, 13.24; S, 10.10. Found: C, 56.40; H, 4.61; N, 12.96; S, 10.27.

EXAMPLE 24

2-(2'-Methoxy-4'-N-methyl-methanesulfonylamino-phenyl)-benzimidazole

Prepared analogously to Example 14 from o-phenylenediamine and 2-methoxy-4-N-methyl-methanesulfonylamino-benzoic acid.

Yield: 21.7% of theory,
M.p.: >250° C.
$C_{16}H_{17}N_3O_3S$ (331.40)
Calc.: C, 57.99; H, 5.17; N, 12.68; S, 9.68. Found: C, 57.98; H, 4.96; N, 12.79; S, 9.53.

EXAMPLE 25

8-(2'-Methoxy-4'-N-ethyl-methanesulfonylamino-phenyl)purine

Prepared analogously to Example 14 from 4,5-diaminopyrimidine and 2-methoxy-4-N-ethyl-methanesulfonylamino-benzoic acid.

Yield: 13.8% of theory,
M.p.: 246°–248° C.
$C_{15}H_{17}N_5O_3S$ (347.41)
Calc.: C, 51.85; H, 4.93; N, 20.16; S, 9.23. Found: C, 51.83; H, 4.78; N, 19.90; S, 9.46.

$^1$H-NMR spectrum (DMSO-$d_6$/CD$_3$OD): $\delta$=1.0–1.3 (t, 3H); 3.1 (s, 3H); 3.6–4.0 (q, 2H); 4.1 (s, 3H); 7.1–7.3 (m, 2H); 8.2–8.4 (d, 1H); 8.8 (s, 1H); 9.0 (s, 1H) ppm.

EXAMPLE 26

5-Methoxy-2-(2'-methoxy-4'-methanesulfonylamino-phenyl)-benzimidazole

Prepared analogously to Example 14 from 4-methoxy-o-phenylenediamine and 2-methoxy-4-methanesulfonylamino-benzoic acid.

Yield: 28.8% of theory,
M.p.: 195°–198° C.
$C_{16}H_{17}N_3O_4S$ (347.40)
Calc.: C, 55.32; H, 4.93; N, 12.10; S, 9.23. Found: C, 55.54; H, 5.34; N, 11.93; S, 8.70.

EXAMPLE 27

5-Chloro-2-(2'-methoxy-4'-methanesulfonylamino-phenyl)-benzimidazole

Prepared analogously to Example 14 from 4-chloro-o-phenylenediamine and 2-methoxy-4-methanesulfonylamino-benzoic acid.

Yield: 43.8% of theory,
M.p.: 230°–232° C.
$C_{15}H_{14}ClN_3O_3S$ (351.82)
Calc.: C, 51.21; H, 4.01; N, 11.94; Cl, 10.08; S, 9.11. Found: C, 51.27; H, 4.02; N, 11.87; Cl, 10.15; S, 9.00.

EXAMPLE 28

5-Chloro-2-(2'-methoxy-4'-N-methyl-methanesulfonylaminophenyl)-benzimidazole

Prepared analogously to Example 14 from 4-chloro-o-phenylenediamine and 2-methoxy-4-N-methyl-methanesulfonylamino-benzoic acid.

Yield: 28.8% of theory,
M.p. 191°–192° C.
$C_{16}H_{16}ClN_3O_3S$ (365.85)
Calc.: C, 52.53; H, 4.41; N, 11.49; Cl, 9.69; S, 8.76. Found: C, 52.95; H, 4.52; N, 11.45; Cl, 9.86; S, 8.82.

EXAMPLE 29

2-(2'-Methoxy-4'-methylthiomethyl-phenyl)-imidazo[4,5-b]pyridine

Prepared analogously to Example 14 from 2,3-diaminopyridine and 2-methoxy-4-methylthiomethyl-benzoic acid.

Yield: 35.1% of theory,
M.p.: 148°–149° C.
$C_{15}H_{15}N_3OS$ (285.35)
Calc.: C, 63.14; H, 5.30; N, 14.73; S, 11.24. Found: C, 62.72; H, 5.53; N, 14.47; S, 10.84.

EXAMPLE 30

8-(2'-Methoxy-(4-methylthiomethyl-phenyl)-purine

Prepared analogously to Example 14 from 4,5-diaminopyrimidine and 2-methoxy-4-methylthiomethyl-benzoic acid.

Yield: 31.4% of theory,
M.p.: 194°–196° C.
$C_{14}H_{14}N_4OS$ (286.36)
Calc.: C, 58.72; H, 4.93; N, 19.57. Found: C, 58.48; H, 4.87; N, 19.29.

EXAMPLE 31

2-(2'-Methoxy-4'-methylsulfonylmethyl-phenyl)-imidazo[4,5-b]pyridine

An amount of 1.4 gm (4.9 mmol) of 2-(2'-methoxy-4'-methylthiomethyl-phenyl)-imidazo[4,5-b]pyridine was dissolved in 30 ml of glacial acetic acid and mixed with 3 ml of 30% hydrogen peroxide. After 48 hours at ambient temperature the solution was diluted with 200 ml of water, made alkaline with concentrated ammonia solution, saturated with sodium chloride, and extracted three times with 30 ml of methylene chloride. The organic extracts were concentrated by evaporation, and the solid residue was purified by column chromatography (200 gm of silica gel; eluant: methylene chloride with 1 to 3% of ethanol).

Yield: 18.6% of theory,
M.p.: 224°–225° C.
$C_{15}H_{15}N_3O_3S$ (317.38)
Calc.: C, 56.77; H, 4.76; N, 13.24; S, 10.10. Found: C, 56.23; H, 4.78; N, 12.97; S, 9.68.

EXAMPLE 32

8-(2'-Methoxy-4'-methylsulfonylmethyl-phenyl)-purine

Prepared analogously to Example 31 from 8-(2'-methoxy-4'-methyl-thiomethyl-phenyl)-purine and peracetic acid.

Yield: 43.6% of theory,
M.p.: 235°–237° C.
$C_{14}H_{14}N_4O_3S$ (318.36)
Calc.: C, 52.82; H, 4.43; N, 17.60. Found: C, 52.74; H, 4.60; N, 16.81.

EXAMPLE 33

2-(2'-Methoxy-4'-methylsulfinylmethyl-phenyl)-imidazo[4,5-b]pyridine

A quantity of 1.4 gm (4.9 mmol) of 2-(2'-methoxy-4'-methylthiomethyl-phenyl)-imidazo[4,5-b]pyridine was dissolved in 30 ml of glacial acetic acid and mixed with 3 ml of 30% hydrogen peroxide. After stirring for two hours at ambient temperature, the solution was diluted with 200 ml of water, made alkaline with concentrated ammonia solution, saturated with sodium chloride, and extracted three times with 30 ml of methylene chloride. The organic extracts were concentrated by evaporation, and the solid residue was purified by column chromatography (200 gm of silica gel; eluant: methylene chloride with 2 to 10% of ethanol).

Yield: 21.7% of theory.
$C_{15}H_{15}N_3O_2S$ (301.38)
Calc.: C, 59.78; H, 5.02; N, 10.64. Found: C, 59.42; H, 5.54; N, 11.53.

$^1$H-NMR spectrum (CDCl$_3$/CD$_3$OD): $\delta$=2.6 (s, 3H); 4.1 (s, 5H); 6.9–7.4 (m, 3H); 7.8–8.0 (m, 1H); 8.2–8.4 (m, 2H) ppm.

EXAMPLE 34

8-(2'-Methoxy-4'-methylsulfinylmethyl-phenyl)-purine

Prepared analogously to Example 33 from 8-(2'-methoxy-4'-methyl-thiomethyl-phenyl)-purine and peracetic acid.

Yield: 53.7% of theory.
R$_f$ value: 0.18 [silica gel; eluant:methylene chloride/ethanol (9:1)].

$^1$H-NMR spectrum (CDCl$_3$/CD$_3$OD): $\delta$=2.6 (s, 3H); 4.1 (s, 5H); 7.0–7.3 (m, 2H); 8.3–8.6 (m, 1H); 8.8–9.1 (m, 2H) ppm.

EXAMPLE 35

2-(2'-Methoxy-4'-cyano-phenyl)-imidazo[4,5-b]pyridine

Quantities of 3.1 gm of 2,3-diaminopyridine and 5.0 gm of 2-methoxy-4-cyano-benzoic acid were refluxed for 2.5 hours in 50 ml of phosphorus oxychloride. After cooling, the reaction mixture was treated with ice water. The precipitate obtained was washed with water and dried at 60° C. in a circulating air drier, after which the product still contained barely half a mol of hydrochloric acid and half a mol of water.

Yield: 6.3 gm (80% of theory),
M.p.: 214°–216° C. (decomposition).
Calc. (for 0.5 mol of HCl and 0.5 mol of H$_2$O): C, 60.59; H, 4.18; N, 20.19; Cl, 6.38. Found: C, 60.85; H, 4.15; N, 20.48; Cl, 6.35.

EXAMPLE 36

2-(2'-Methoxy-4'-carboxy-phenyl)-imidazo[4,5-b]pyridine

An amount of 3.9 gm of 2-(2'-methoxy-4'-cyano-phenyl)-imidazo[4,5-b]pyridine was refluxed in 70 ml of 2N aqueous sodium hydroxide solution, under stirring, for ten minutes, during which the starting material went into solution. The mixture was cooled to about 50° C. and filtered over active charcoal. After cooling to ambient temperature, the mixture was acidified with glacial acetic acid, and the precipitate obtained was subjected to suction filtration and washed with water. Finally, it was crystallized from ethylene glycol, with the addition of active charcoal, and the crystals precipitated were washed with ethanol and acetone.

Yield: 2.3 gm (55% of theory),
M.p.: 309°–310° C.
Calc.: C, 62.45; H, 4.12; N, 15.61. Found: C, 62.30; H, 4.47; N, 15.60.

EXAMPLE 37

2-(2'-Methoxy-4'-methoxycarbonyl-phenyl)-imidazo[4,5-b]pyridine hydrochloride

Three grams of 2-(2'-methoxy-4'-carboxy-phenyl)-imidazo[4,5-b]pyridine were refluxed with 40 ml of thionyl chloride for three hours and then concentrated to dryness in vacuo. The residue was boiled in 200 ml of methanol, the solution was filtered over active charcoal, and the precipitate obtained after cooling was subjected to filtration and washed with methanol and ether.

Yield: 2.4 gm (68% of theory),
M.p.: 238°–239° C. (decomposition).
Calc.: C, 56.34; H, 4.41; N, 13.14; Cl, 11.09. Found: C, 55.96; H, 4.50; N, 13.30; Cl, 11.75.

EXAMPLE 38

2-(2'-Methoxy-4'-aminocarbonyl-phenyl)-imidazo[4,5-b]pyridine hydrochloride

Three grams of the acid chloride hydrochloride obtained from 2-(2'-carboxy-phenyl)-imidazo[4,5-b]pyridine and thionyl chloride by boiling for 1.5 hours and evaporation to dryness were suspended in 70 ml of dioxane, and 10 ml of a concentrated aqueous ammonia solution were slowly added thereto dropwise. The resulting mixture was stirred for 30 minutes at 80° C., the dioxane was substantially distilled off, the residue was stirred with water, and the product precipitated was subjected to suction filtration. It was recrystallized from a mixture of 120 ml of ethanol and 120 ml of 2N hydrochloric acid.

Yield: 1.7 gm (60% of theory),
M.p.: >280° C.
Calc.: C, 55.18; H, 4.30; N, 18.39; Cl, 11.63. Found: C, 55.36; H, 4.46; N, 18.29; Cl, 11.76.

EXAMPLE 39

2-(2'-Methoxy-4'-methylaminocarbonyl-phenyl)-imidazo[4,5-b]pyridine

Prepared analogously to Example 38 form the corresponding acid chloride hydrochloride and methylamine.

Yield: 54% of theory,
M.p.: 263°–265° C. (from ethanol).
Calc: C, 63.82; H, 5.00; N, 19.85. Found: C, 63.50; H, 5.38; N, 19.59.

EXAMPLE 40

2-(2'-Methoxy-4'-dimethylaminocarbonyl-phenyl)-imidazo[4,5-b]pyridine hydrochloride Prepared analogously to Example 38 from the corresponding acid chloride hydrochloride and dimethylamine. The hydrochloride was precipitated from acetone with ethereal hydrochloric acid and recrystallized from ethanol/ethyl acetate.

Yield: 52% of theory,
M.p.: 232° C. (decomposition).
Calc.: C, 57.75; H, 5.15; N, 16.84; Cl, 10.85. Found: C, 57.50; H, 5.46; N, 16.65; Cl, 10.94.

EXAMPLE 41

8-(2'-Methoxy-4'-cyano-phenyl)-purine

Prepared analogously to Example 35 from 4,5-diaminopyrimidine (crystals obtained from dihydrochloride with 1 mol of common salt) and 2-methoxy-4-cyano-benzoic acid.

Yield: 0.7 gm (20% of theory),
M.p.: 271°–272° C. (from methanol).
Calc.: C, 62.14; H, 3.61; N, 27.88. Found: C, 62.34; H, 3.69; N, 27.62.

EXAMPLE 42

8-(2'-Methoxy-4'-carboxy-phenyl)-purine

Prepared by refluxing a solution of 1.45 gm of 8-(2'-methoxy-4'-cyano-phenyl)-purine in 100 ml of 25% sodium hydroxide solution for four hours. The product was worked up as in Example 36 but without recrystallization.

Yield: 1.3 gm (96% of theory),
M.p.: >250° C.
Calc.: C, 57.78; H, 3.73; N, 20.73. Found: C, 57.40, H, 3.85; N, 20.84.

EXAMPLE 43

8-(2'-Methoxy-4'-aminocarbonyl-phenyl)-purine

Two grams of 8-(2'-methoxy-4'-carboxy-phenyl)-purine were refluxed for three hours with 100 ml of thionyl chloride. Excess thionyl chloride was distilled off, and then the residue was evaporated three times with methylene chloride. The remaining acid chloride hydrochloride was suspended in 125 ml of dioxane, and 10 ml of concentrated aqueous ammonia solution were added dropwise, under stirring. The suspension was heated for one hour over a steam bath, so that a clear solution formed. The solvent was evaporated off, and the crystalline residue was triturated with water, subjected to suction filtration, treated with warm aqueous sodium carbonate solution, washed with water, and dried.

Yield: 0.53 gm (26% of theory),
M.p.: >250° C.

Calc.: C, 56.86; H, 4.50; N, 25.85. Found: C, 57.15; H, 4.25; N, 25.61.

EXAMPLE 44

8-(2'-Methoxy-4'-methylaminocarbonyl-phenyl)-purine

Forty milliliters of ethanolic methylamine solution were added to 0.42 gm of 8-(2'-methoxy-4'-chlorocarbonyl-phenyl)-purine hydrochloride (see Example 43), with cooling, and the mixture was refluxed for 30 minutes. It was then concentrated by evaporation, and the product was purified by column chromatography on silica gel [eluant:methylene chloride/ethanol (8:2)].

Yield: 0.19 gm (45% of theory),
M.p.: >250° C.
Calc.: C, 59.36; H, 4.63, N, 24.72. Found: C, 58.98; H, 4.66; N, 24.55.

EXAMPLE 45

8-(2'-Methoxy-4'-ethoxycarbonyl-phenyl)-purine

A quantity of 0.42 gm of 8-(2'-methoxy-4'-chlorocarbonyl-phenyl)-purine hydrochloride (see Example 43) was refluxed in 30 ml of ethanol for 45 minutes. The solvent was evaporated off, and the residue was purified over a silica gel column [eluant:methylene chloride/ethanol (50:1 to 19:1)].

Yield: 0.18 gm (40% of theory),
M.p.: 210°–212° C.
Calc.: C, 60.40; H, 4.73; N, 18.78. Found: C, 60.11; H, 4.82; N, 18.87.

EXAMPLE 46

8-(2'-Methoxy-4'-aminocarbonyl-phenyl)-purine

One gram of 8-(2'-methoxy-4'-cyano-phenyl)-purine was dissolved in 75 ml of 2N sodium hydroxide solution and refluxed for 15 minutes. Then, the mixture was acidified with hydrochloric acid, and the mixture precipitated was separated into its components by use of silica gel [eluant:methylene chloride/ethanol (7:3 to 1:1)].

Yield: 0.1 gm (10% of theory),
M.p.: >250° C.

In addition, 0.4 gm (39% of theory) of the corresponding carboxylic acid were obtained.

EXAMPLE 47

2-(2'-Methoxy-4'-dimethylaminosulfonyl-phenyl)-imidazo[4,5-b]pyridine hydrochloride The crude 2-(2'-methoxy-4'-chlorosulfonyl-phenyl)-imidazo[4,5-b]pyridine hydrochloride prepared from 2.5 gm of 2-methoxy-4-chlorosulfonyl-benzoic acid according to Example C was added to 150 ml of a saturated aqueous dimethylamine solution at 10° C., under stirring, and a light-colored precipitate formed slowly. After stirring for 20 hours at ambient temperature, 200 ml of ice water were added. The precipitate was dried and then taken up in 60 ml of methanol, and 10 ml of methanolic hydrochloric acid were added. After filtering over active charcoal, the solvent was eliminated, and the residue remaining was digested with acetone and ether, subjected to suction filtration, and washed with ether.

Yield: 0.55 gm (15% of theory),
M.p.: 205°–210° C.
Calc.: C, 48.84; H, 4.65; N, 15.19; Cl, 9.16; S, 8.69. Found: C, 48.56; H, 4.53; N, 15.09; Cl, 9.44; S, 8.69.

EXAMPLE 48

2-(2'-Methoxy-4'-methylaminosulfonyl-phenyl)-imidazo[4,5-b]pyridine hydrochloride Prepared analogously to Example 47 from 2-(2'-methoxy-4'-chlorosulfonyl-phenyl)-imidazo[4,5-b]pyridine hydrochloride and 40% aqueous methylamine solution. After the addition of ice water, the mixture was extracted with ethyl acetate and concentrated by evaporation, and the residue was processed further as in Example 47, to form a hemihydrate.

Yield: 19% of theory,
M.p.: 205°–207° C. (decomposition).
Calc.: C, 46.22; H, 4.73; N, 15.40; Cl, 9.75; S, 8.81. Found: C, 46.19; H, 4.86; N, 15.00; Cl, 10.08; S, 8.52.

The aqueous phases obtained when the ethyl acetate phases were washed were left to stand overnight, and a further fraction of the product was obtained in the form of a free base.

Yield: 10% of theory,
M.p.: 246°–247° C. (decomposition).
Calc.: C, 52.81; H, 4.43; N, 17.60; S, 10.07. Found: C, 52.92; H, 4.43; N, 17.48; S, 10.27.

EXAMPLE 49

2-(2'-Methoxy-4'-aminosulfonyl-phenyl)-imidazo[4,5-b]pyridine hydrochloride

Prepared analogously to Example 47 starting from 2-methoxy-4-chlorosulfonyl-benzoic acid, ammonia, and 2,3-diamino-pyridine.

Yield: 16.4% of theory,
M.p.: 225° C.
Calc.: C, 45.82; H, 3.85; N, 16.44; Cl, 10.40; S, 9.41. Found: Cl 45.67; H, 4.11; N, 16.24; Cl, 10.15; S, 9.18.

EXAMPLE 50

8-(2'-Methoxy-4'-aminosulfonyl-phenyl)-purine

Prepared analogously to Example 47 from 2-methoxy-4-chlorosulfonyl-benzoic acid, ammonia, and 4,5-diaminopyrimidine (crystals obtained from the dihydrochloride with 1 mol or common salt). After being reacted with aqueous ammonia, the reaction solution was evaporated down to about one-third, after which the free base was precipitated in the form of crystals.

Yield: 65% of theory,
M.p.: 270° C. (decomposition).
Calc.: C, 47.21; H, 3.63; N, 22.94; S, 10.50. Found: C, 46.95; H, 3.68; N, 22.84; S, 10.50.

EXAMPLE 51

8-(2'-Methoxy-4'-methylaminosulfonyl-phenyl)-purine hydrochloride

Prepared analogously to Example 50 from 2-methoxy-4-chlorosulfonyl-benzoic acid, aqueous methylamine solution, and 4,5-diamino-pyrimidine. The crude free base was converted into the hydrochloride with 2N hydrochloride acid, and the hydrochloride was purified by boiling with methanol.

Yield: 15% of theory,
M.p.: 243° C. (decomposition).
Calc.: C, 43.88; H, 3.97; N, 19.68; Cl, 9.97; S, 9.01. Found: C, 43.96; H, 4.04; N, 19.67; Cl, 9.86; S, 8.98.

EXAMPLE 52

8-(2'-Methoxy-4'-dimethylaminosulfonyl-phenyl)-purine hydrochloride

Prepared analogously to Example 51 from 2-methoxy-4-chlorosulfonyl-benzoic acid, aqueous dimethylamine solution, and 4,5-diamino-pyrimidine. The hydrochloride was recrystallized from ethanol/water (4:1).

Yield: 27% of theory,
M.p.: 230°–234° C.
Calc.: C, 45.47; H, 4.36; N, 18.94; Cl, 9.60; S, 8.70.
Found: C, 45.11; H, 4.66; N, 19.26; Cl, 9.24; S, 8.43.

EXAMPLE 53

8-[2'-Methoxy-4'-(4-morpholinyl-sulfonyl)-phenyl]-purine

An amount of 0.8 ml of morpholine was dissolved in a two-phase mixture of 40 ml of ethyl acetate and 40 ml of water. Then, 1 gm of crude 8-(2'-methoxy-4'-chlorosulfonylphenyl)-purine hydrochloride was added thereto in batches, under vigorous stirring, and the resulting mixture was heated to 80° C. for two hours. The reaction mixture was concentrated down to one-third of the volume, and the crystals precipitated were subjected to suction filtration and washed with water.

Yield: 0.3 gm (30% of theory),
M.p.: >250° C.
Calc.: C, 51.20; H, 4.56; N, 18.66; S, 8.54. Found: C, 51.00; H, 4.56; N, 18.40; S, 8.80.

EXAMPLE 54

8-(2'-Methoxy-4'-n-butylaminosulfonyl-phenyl)-purine

Prepared analogously to Example 51 from n-butylamine and 8-(2'-methoxy-4'-chlorosulfonyl-phenyl)-purine hydrochloride. After the reaction finished, the aqueous phase wsa extracted with ethyl acetate. The residue remaining after the ethyl acetate phases were evaporated was digested with ethanol, subjected to suction filtration, and washed with water.

Yield: 0.27 gm (28% of theory),
M.p.: 212°–214° C. (decomposition).
Calc.: C, 53.17; H, 5.30; N, 19.30; S, 8.87. Found: C, 53.43; H, 5.46; N, 19.00; S, 8.51.

EXAMPLE 55

2-(2'-Dimethylamino-4'-nitro-phenyl)-imidazo[4,5-b]pyridine

A quantity of 6.3 gm of 2-dimethylamino-4-nitro-benzoic acid was finely triturated with 5.43 gm of 2,3-diamino-pyridine dihydrochloride, mixed with 125 ml of phosphorus oxychloride, and refluxed for two hours. Excess phosphorus oxychloride was largely distilled off in vacuo, and the residue was mixed with ice water and then neutralized with ammonia. The solid product precipitated was purified by column chromatography on silica gel [eluant:first methylene chloride, then methylene chloride/ethanol (50:1 to 25:1)].

Yield: 2.2 gm (26% of theory),
M.p.: 208°–210° C.
Calc.: C, 59.36; H, 4.63; N, 24.72. Found: C, 59.40; H, 4.50; N, 25.10.

EXAMPLE 56

2-(2'-Dimethylamino-4'-methanesulfonylamino-phenyl)-imidazo[4,5-b]pyridine

An amount of 0.49 gm 2-(2'-dimethylamino-4'-aminophenyl)-imidazo[4,5-b]pyridine dihydrochloride was dissolved in 10 ml of pyridine, 0.38 gm of methanesulfonyl chloride were added dropwise, and the mixture was stirred for two days at ambient temperature. The reaction mixture was poured onto water, and the solution obtained was extracted with ethyl acetate. The ethyl acetate phases were washed with common salt solution and concentrated by evaporation. The residue was triturated with 2N acetic acid, subjected to filtration, and washed with water.

Yield: 0.32 gm (65% of theory),
M.p.: 265°–267° C.
Calc.: C, 54.38; H, 5.17; N, 21.14; S, 9.66. Found: C, 54.10; H, 5.08; N, 21.03; S, 9.12.

EXAMPLE 57

2-(2'-Dimethylamino-4'-methanesulfonyloxy-phenyl)-imidazo[4,5-b]pyridine

Prepared analogously to Example 56 from 2-(2'-dimethylamino-4'-hydroxy-phenyl)-imidazo[4,5-b]pyridine dihydrochloride and methanesulfonyl chloride. The product was purified over silica gel column [eluant:first methylene chloride, then methylene chloride/ethanol (50:1)].

Yield: 56% of theory,
M.p.: 197°–199° C.
Calc.: C, 54.22; H, 4.85; N, 16.86; S, 9.67. Found: C, 54.31; H, 4.89; N, 16.61; S, 9.47.

EXAMPLE 58

5-Acetamino-2-(2'-methoxy-4'-methanesulfonyloxy-phenyl)-benzimidazole

Prepared analogously to Example 1 from 5-acetamino-2-(2'-methoxy-4'-hydroxy-phenyl)-benzimidazole and methanesulfonic acid chloride.

Yield: 46% of theory,
M.p.: 220°–222° C.
$C_{17}H_{17}N_3O_3S$ (375.41)
Calc.: C, 54.39; H, 4.56; N, 11.19; S, 8.54. Found: C, 54.20; H, 4.50; N, 11.07; S, 8.40.

EXAMPLE 59

5,6-Dimethyl-2-(2'-methoxy-4'-methanesulfonyloxy-phenyl)-benzimidazole

Prepared analogously to Example 1 from 5,6-dimethyl-2-(2'-methoxy-4'-hydroxy-phenyl)-benzimidazole and methanesulfonic acid chloride.

Yield: 39% of theory,
M.p.: 175°–176° C.
$C_{17}H_{18}N_2O_4S \times H_2O$ (364.43) Calc.: C, 56.02; H, 5.53; N, 7.69. Found. C, 56.02, H, 5.80; N, 6.98.

EXAMPLE 60

2-(2'-Methoxy-4'-methanesulfonyloxy-phenyl)-imidazo[4,5-c]pyridine

Prepared analogously to Example 1 from 2-(2'-methoxy-4'-hydroxy-phenyl)-imidazo[4,5-c]pyridine and methanesulfonic acid chloride.

Yield: 66.3% of theory,
M.p.: 208°–210° C.
$C_{14}H_{13}N_3O_4S$ (319.35) Calc.: C, 52.66; H, 4.10; N, 13.16. Found: C, 52.60; H, 4.21; N, 13.10.

EXAMPLE 61

5-Methoxycarbonyl-2-(2'-methoxy-4'-methanesulfonyloxy-phenyl)-benzimidazole

Prepared analogously to Example 1 from 5-methoxycarbonyl-2-(2'-methoxy-4'-hydroxy-phenyl)-benzimidazole and methanesulfonic acid chloride.
Yield: 35% of theory,
M.p.: 121°–123° C.
$C_{17}H_{16}N_2O_6S \times H_2O$ (394.42) Calc.: C, 51.76; H, 4.60; N, 7.10. Found: C, 52.03; H, 4.56; N, 7.14.

EXAMPLE 62

5-Methanesulfonylamino-2-(2'-methoxy-4'-methanesulfonyloxyphenyl)-benzimidazole

Prepared analogously to Example 1 from 5-amino-2-(2'-methoxy-4'-hydroxy-phenyl)-benzimidazole and methanesulfonic acid chloride.
Yield: 6% of theory,
M.p.: 240° C. (decomposition).
$C_{16}H_{17}N_3O_6S_2$ (411.47)
Calc.: C, 46.70; H, 4.16; N, 10.21. Found: C, 46.63; H, 4.25; N, 10.16.

EXAMPLE 63

5-Methoxycarbonylamino-2-(2'-methoxy-4'-methanesulfonyloxyphenyl)-benzimidazole

Prepared analogously to Example 1 from 5-methoxycarbonylamino-2-(2'-methoxy-4'-hydroxy-phenyl)-benzimidazole and methanesulfonic acid chloride.
Yield: 37.3% of theory,
M.p.: 140° C. (decomposition).
$C_{17}H_{17}N_3O_6S \times H_2O$ (409.42)
Calc.: C, 49.87; H, 4.67; N, 10.26; S, 7.83. Found: C, 50.32; H, 4.70; N, 10.49; S, 7.85.

EXAMPLE 64

5-Methyl-2-(2'-methoxy-4'-methanesulfonyloxy-phenyl)-benzimidazole

Prepared analogously to Example 1 from 5-methyl-2-(2'-methoxy-4'-hydroxy-phenyl)-benzimidazole.
Yield: 30.6% of theory,
M.p.: 130°–133° C.
Calc.: C, 57.81; H, 4.85; N, 8.43; S, 9.65. Found: C, 57.66; H, 5.04; N, 8.40; S, 9.54.

EXAMPLE 65

5-Fluoro-2-(2'-methoxy-4'-methanesulfonyloxy-phenyl)-benzimidazole

Prepared analogously to Example 1 from 5-fluoro-2-(2'-methoxy-4'-hydroxy-phenyl)-benzimidazole and methanesulfonic acid chloride.
Yield: 71% of theory,
M.p.: 203°–204° C.
$C_{15}H_{13}FN_2O_4S$ (336.35)
Calc.: C, 53.56; H, 3.90; N, 8.33; S, 9.53. Found: C, 53.40; H, 3.97; N, 8.75; S, 9.61.

EXAMPLE 66

2-(2'-Methoxy-4'-trifluoromethanesulfonyloxy-phenyl)-benzimidazole

Prepared analogously to Example 1 from 2-(2'-methoxy-4'-hydroxyphenyl)-benzimidazole and trifluoromethanesulfonic acid anhydride.
Yield: 44.6% of theory,
M.p.: 191°–193° C.
$C_{15}H_{11}F_3N_2O_4S$ (372.3)
Calc.: C, 48.39; H, 2.98; N, 7.53; S, 8.61. Found: C, 48.08; H, 3.20; N, 7.48; S, 9.06.

EXAMPLE 67

2-(2'-Methoxy-4'-trifluoromethanesulfonyloxy-phenyl)-imidazo[4,5-b]pyridine

Prepared analogously to Example 1 from 2-(2'-methoxy-4'-hydroxyphenyl)-imidazo[4,5-b]pyridine and trifluoromethanesulfonic acid anhydride.
Yield: 53.8% of theory,
M.p.: 205°–207° C.
$C_{14}H_{10}F_3N_3O_4S$ (373.3)
Calc.: C, 45.05; H, 2.70; N, 11.26. Found: C, 45.29; H, 2.75; N, 11.38.

EXAMPLE 68

8-(2'-n-Propyl-4'-methanesulfonyloxy-phenyl)-purine

Prepared analogously to Example 1 from 8-(2'-n-propyl-4'-hydroxy-phenyl)-purine and methanesulfonic acid chloride.
Yield: 64.1% of theory,
M.p.: 214°–216° C.
$C_{15}H_{16}N_4O_3S$ (332.4)
Calc.: C, 54.20; H, 4.85; N 16.86. Found: C, 54.45; H, 4.77; N 17.00.

EXAMPLE 69

8-(2'-Methoxy-4'-trifluoromethanesulfonyloxy-phenyl)-purine

Prepared analogously to Example 1 from 8-(2'-methoxy-4'-hydroxy-phenyl)-purine and trifluoromethanesulfonic acid anhydride.
Yield: 37.4% of theory,
M.p.: 228°–229° C.
$C_{13}H_9F_3N_4O_4S$ (374.3)
Calc.: C, 41.72; H, 2.42; N, 14.97. Found: C, 41.75; H, 2.50; N, 15.20.

EXAMPLE 70

8-(2'-Ethyl-4'-methanesulfonyloxy-phenyl)-purine

Prepared analogously to Example 1 from 8-(2'-ethyl-4'-hydroxyphenyl)-purine and methanesulfonic acid chloride.
Yield: 69.2% of theory,
M.p.: 237°–238° C.
$C_{14}H_{14}N_4O_3S$ (318.4)
Calc.: C, 52.81; H, 4.43; N, 17.60. Found: C, 53.00; H, 4.39; N, 17.70.

EXAMPLE 71

6-Methyl-2-(2'-methoxy-4'-methanesulfonyloxy-phenyl)-imidazo[4,5-b]pyridine

Prepared analogously to Example 1 from 6-methyl-2-(2'-methoxy-4'-hydroxy-phenyl)-imidazo[4,5-b]pyridine and methanesulfonic acid chloride.
Yield: 38.6% of theory,
M.p.: 185°–187° C.
$C_{15}H_{15}N_3O_4S$ (333.4)
Calc.: C, 54.04; H, 4.54; N, 12.60; S, 9.62. Found: C, 54.04; H, 4.55; N, 12.68; S, 9.50.

EXAMPLE 72

5-Nitro-2-(2'-methoxy-4'-N-methyl-methanesulfonylaminophenyl)-benzimidazole hydrochloride Prepared analogously to Example 14 from 4-nitro-1,2-phenylenediamine and 2-methoxy-4-N-methyl-methanesulfonylamino-benzoic acid.

Yield: 52.1% of theory,
M.p.: 241°–243° C.
$C_{16}H_{16}N_4O_5S \times HCl$ (412.87)
Calc.: C, 46.55; H, 4.15; N, 13.56; S, 7.77; Cl, 8.58. Found: C, 46.75; H, 3.94; N, 13.68; S, 7.72; Cl, 8.29.

EXAMPLE 73

5-Methoxy-2-(2'-methoxy-4'-N-methyl-methanesulfonylaminophenyl)-benzimidazole

Prepared analogously to Example 14 from 4-methoxy-1,2-phenylenediamine and 2-methoxy-4-N-methyl-methanesulfonylamino-benzoic acid.

Yield: 33.7% of theory,
M.p.: 194°–196° C.
$C_{17}H_{19}N_3O_4S$ (361.43)
Calc.: C, 56.49; H, 5.30; N, 11.63; S, 8.87. Found: C, 56.49; H, 5.40; N, 11.73; S, 8.84.

EXAMPLE 74

5-Trifluoromethyl-2-(2'-methoxy-4'-N-methyl-methanesulfonylamino-phenyl)-benzimidazole Prepared analogously to Example 14 from 4-trifluoromethyl-1,2-phenylenediamine and 2-methoxy-4-N-methyl-methanesulfonylamino-benzoic acid.

Yield: 6.7% of theory,
M.p.: 222°–225° C.
$C_{17}H_{16}F_3N_3O_3S$ (399.41)
Calc.: C, 51.12; H, 4.04; N, 10.52; S, 8.02. Found: C, 51.34; H, 4.38; N, 10.28; S, 8.47.

EXAMPLE 75

5-Trifluoromethyl-2-(2'-methoxy-4'-methanesulfonylaminophenyl)-benzimidazole

Prepared analogously to Example 14 from 4-trifluoromethyl-1,2-phenylenediamine and 2-methoxy-4-methanesulfonylamino-benzoic acid.

Yield: 24.9% of theory,
M.p.: 115°–118° C.
$C_{16}H_{14}F_3N_3O_3S$ (385.33)
Calc.: C, 49.87; H, 3.66; N, 10.90 S, 8.32. Found: C, 49.64; H, 3.89; N, 10.65 S, 8.34.

EXAMPLE 76

5-Nitro-2-(2'-methoxy-4'-methanesulfonylaminophenyl)-benzimidazole dihydrochloride Prepared analogously to Example 14 from 4-nitro-1,2-phenylenediamine and 2-methoxy-4-methanesulfonylamino-benzoic acid.

Yield: 14.0% of theory,
M.p.: 240°–243° C.
$C_{15}H_{14}N_4O_5S \times H_2O \times 2\ HCl$ (453.33)
Calc.: C, 39.74; H, 4.00; N, 12.36. Found: C, 39.56; H, 4.06; N, 12.40.

EXAMPLE 77

5,6-Dimethyl-2-(2'-methoxy-4'-N-methyl-methanesulfonylaminophenyl)-benzimidazole Prepared analogously to Example 14 from 4,5-dimethyl-1,2-phenylenediamine and 2-methoxy-4-N-methyl-methanesulfonylamino-benzoic acid.

Yield: 52.3% of theory,
M.p.: 235°–238° C.
$C_{18}H_{21}N_3O_3S$ (359.46)
Calc.: C, 60.14; H, 5.88; N, 11.69; S, 8.92. Found: C, 59.80; H, 5.68; N, 11.75; S, 8.86.

EXAMPLE 78

5,6-Dimethyl-2-(2'-methoxy-4'-methanesulfonylaminophenyl)benzimidazole semihydrochloride Prepared analogously to Example 14 from 4,5-dimethyl-1,2-phenylenediamine and 2-methoxy-4-methanesulfonylaminobenzoic acid.

Yield: 25.6% of theory,
M.p.: 148°–151° C.
$C_{17}H_{19}N_3O_3S \times \frac{1}{2}HCl$ (363.67)
Calc.: C, 56.14; H, 5.54; N, 11.55. Found: C, 56.26; H, 5.76; N, 11.68.

EXAMPLE 79

5,6-Dimethoxy-2-(2'-methoxy-4'-N-methyl-methanesulfonylaminophenyl)-benzimidazole hydrochloride Prepared analogously to Example 14 from 4,5-dimethoxy-1,2-phenylenediamine and 2-methoxy-4-N-methyl-methanesulfonylamino-benzoic acid.

Yield: 21% of theory,
M.p.: >250° C.
$C_{18}H_{21}N_3O_5S \times HCl$ (427.93)
Calc.: C, 50.52; H, 5.18; N, 9.82. Found: C, 50.30; H, 5.10; N, 9.89.

EXAMPLE 80

5,6-Dimethoxy-2-(2'-methoxy-4'-methanesulfonylamino-phenyl)-benzimidazole

Prepared analogously to Example 14 from 4,5-dimethoxy-1,2-phenylenediamine and 2-methoxy-4-methanesulfonylamino-benzoic acid.

Yield: 27.8% of theory,
M.p.: >250° C.
$C_{17}H_{19}N_3O_5S$ (377.49)
Calc.: C, 54.09; H, 5.07; N, 11.13. Found: C, 53.84; H, 5.32; N, 10.78.

EXAMPLE 81

5-Methoxycarbonyl-2-(2'-methoxy-4'-methanesulfonylaminophenyl)-benzimidazole

Prepared analogously to Example 14 from 4-methoxycarbonyl-1,2-phenylenediamine and 2-methoxy-4-methanesulfonylamino-benzoic acid.

Yield: 46.3% of theory,
M.p.: 246°–248° C.
$C_{17}H_{17}N_3O_5S$ (375.41)
Calc.: C, 54.39; H, 4.56; N, 11.19. Found: C, 53.98; H, 4.72; N, 10.93.

EXAMPLE 82

5-Fluoro-2-(2'-methoxy-4'-methanesulfonylaminophenyl)benzimidazole

Prepared analogously to Example 14 from 4-fluoro-1,2-phenylenediamine and 2-methoxy-4-methanesulfonylamino-benzoic acid.
Yield: 67.3% of theory,
M.p.: 254°-256° C.
$C_{15}H_{14}FN_3O_3S$ (335.37)
Calc.: C, 53.72; H, 4.20; N, 12.53; S, 9.56. Found: C, 53.83; H, 4.87; N, 12.06; S, 9.25.

EXAMPLE 83

6-Chloro-2-(2'-methoxy-4'-methanesulfonylaminophenyl)-imidazo[4,5-b]pyridine hydrochloride Prepared analogously to Example 14 from 5-chloro-2,3-diaminopyridine and 2-methoxy-4-methanesulfonylamino-benzoic acid.
Yield: 28.3% of theory,
M.p.: >250° C.
$C_{14}H_{13}ClN_4O_3S \times HCl$ (389.3)
Calc.: C, 43.19; H, 3.62; N, 14.39. Found: C, 43.34; H, 4.05; N, 14.80.

EXAMPLE 84

6-Methyl-2-(2'-methoxy-4'-methanesulfonylaminophenyl)-imidazo[4,5-b]pyridine

Prepared analogously to Example 14 from 5-methyl-2,3-diaminopyridine and 2-methoxy-4-methanesulfonylamino-benzoic acid.
Yield: 42.2% of theory,
M.p.: 253°-256° C.
$C_{15}H_{16}N_4O_3S$ (332.4)
Calc.: C, 54.20; H, 4.85; N, 16.86. Found: C, 53.91; H, 4.97; N, 16.51.
$^1$H-NMR spectrum (DMSO-$d_6$/CD$_3$OD): $\delta$=2.5 (s, 3H); 3.2 (s, 3H); 4.1 (s, 3H); 6.9–7.2 (m, 2H); 7.8 (broad s, 1H); 8.2–8.4 (m, 2H) ppm.

The following compound was prepared in analogous manner:

6-Methyl-2-(2'-methoxy-4'-N-ethyl-methanesulfonylaminophenyl)-imidazo[4,5-b]pyridine Prepared from 5-methyl-2,3-diaminopyridine and 2-methoxy-4-N-ethyl-methanesulfonylamino-benzoic acid.
Yield: 37.8% of theory,
$C_{17}H_{20}N_4O_3S$ (360.4)
Calc.: C, 56.65; H, 5.59; N, 15.55. Found: C, 56.99; H, 5.64; N, 15.21.
$^1$H-NMR spectrum (DMSO-$d_6$/CD$_3$OD): $\delta$=1.0–1.3 (t, 3H); 2.5 (s, 3H); 3.1 (s, 3H); 3.6–4.0 (q, 2H); 4.1 (s, 3H); 7.1–7.4 (m, 2H); 7.8–7.9 (broad s, 1H); 8.2–8.5 (m, 2H) ppm.

EXAMPLE 85

6-Methyl-2-(2'-methoxy-4'-N-methyl-methanesulfonylaminophenyl)-imidazo[4,5-b]pyridine Prepared analogously to Example 14 from 5-methyl-2,3-diaminopyridine and 2-methoxy-4-N-methyl-methanesulfonylamino-benzoic acid.
Yield: 46.2% of theory,
M.p.: 246°-248° C.
$C_{16}H_{18}N_4O_3S$ (346.4)
Calc.: C, 55.48; H, 5.24; N, 16.18; S, 9.26. Found: C, 55.26; H, 5.28; N, 16.35; S, 9.14.

EXAMPLE 86

2-(2'-Methoxy-5'-methanesulfonylamino-phenyl)-imidazo[4,5-b]pyridine

Prepared analogously to Example 14 from 2,3-diaminopyridine and 2-methoxy-5-methanesulfonylamino-benzoic acid,
Yield: 14.2% of theory,
M.p.: >250° C.
$C_{14}H_{14}N_4O_3S$ (318.4)
Calc.: C, 52.81; H, 4.43; N, 17.60; S, 10.07. Found: C, 52.73; H, 4.63; N, 17.25; S, 10.79.

EXAMPLE 87

5-Amino-2-(2'-methoxy-4'-methanesulfonyloxyphenyl)-benzimidazole

Five grams (13.3 mmol) of 5-acetamino-2-(2'-methoxy-4'-methanesulfonyloxy-phenyl)-benzimidazole were suspended in 150 ml of concentrated hydrochloric acid and stirred at 80° C. for two hours. After cooling, the crude product precipitated was subjected to suction filtration and chromatographed on 500 gm of aluminium oxide (neutral) (eluant: methylene chloride with 2.5% ethanol).
Yield: 80.5% of theory,
$C_{15}H_{15}N_3O_4S$ (333.38).
Mass spectrum: M+=333 (mol peak)
Calc.: C, 54.04; H, 4.54; N, 12.61. Found: C, 53.98; H, 4.51; N, 12.73.

EXAMPLE 88

5-Hydroxy-2-(2'-methoxy-4'-methanesulfonyloxyphenyl)-benzimidazole

An amount of 3.2 (9.6 mmol) of 5-amino-2-(2'-methoxy-4'-methanesulfonyloxy-phenyl)-benzimidazole was dissolved in 509 ml of glacial acetic acid, and then a solution of 1.38 gm (20 mmol) of sodium nitrite in 5.0 ml of water was added dropwise, under stirring. After one hour, the mixture was diluted with 100 ml of water, and the solution was refluxed for 1.5 hours. Subsequent to cooling, the solution was adjusted to a pH of 5 with concentrated ammonia and extracted three times, each time with 40 ml of methyl ethyl ketone, and the extracts are dried and concentrated by evaporation in vacuo. The oily residue was chromatographed over 500 gm of aluminium oxide (neutral) (eluant: methylene chloride with 8% ethanol).
Yield: 19.6% of theory,
M.p.: 158°-160° C.
$C_{15}H_{14}N_2O_5S$ (334.36)
Calc.: C, 53.88; H, 4.22; N, 8.38; S, 9.59. Found: C, 54.05; H, 4.44; N, 8.10; S, 9.55.

EXAMPLE 89

5-Methylaminocarbonylamino-2-(2'-methoxy-4'-methanesulfonyloxy-phenyl)-benzimidazole One gram (3.0 mmol) of 5-amino-2-(2'-methoxy-4'-methanesulfonyloxy-phenyl)-benzimidazole was dissolved in 30 ml of pure tetrahydrofuran, 2.0 ml of methylisocyanate were added, and the mixture was refluxed. After 15 minutes that solvent and any excess methylisocyanate were evaporated off in vacuo, and the residue obtained was chromatographed over 250 gm of aluminium oxide (neutral) (eluant: methylene chloride with 4% ethanol).

Yield: 61.5% of theory,
$C_{17}H_{18}N_4O_5S$ (390.43).
Calc.: C, 52.30; H, 4.65; N, 14.35; S, 8.21. Found: C, 52.15; H, 4.83; N, 14.46; S, 7.97.

EXAMPLE 90

5-Aminocarbonylamino-2-(2'-methoxy-4'-methanesulfonyloxyphenyl)-benzimidazole

One gram (3.0 mmol) of 5-amino-2-(2'-methoxy-4'-methanesulfonyloxy-phenyl)-benzimidazole were dissolved in 20 ml of pure tetrahydrofuran, and then 2.0 gm of potassium cyanate and 5 ml of 2M acetic acid were added successively. After the mixture refluxed for eight hours, the solvent was evaporated off in vacuo, and the residue was mixed with 10 ml of water and neutralized with 5% sodium bicarbonate solution. The crude product precipitated was subjected to suction filtration and chromatographed over 200 gm of silica gel (eluant: methylene chloride with 8% ethanol).

Yield 34.5% of theory,
$C_{16}H_{16}N_4O_5S$ (376.40).
Calc.: C, 51.06; H, 4.18; N, 14.54; S, 8.32. Found: C, 50.81; H, 4.16; N, 14.29; S, 8.71.

EXAMPLE 91

5-Methylaminocarbonyl-2-(2'-methoxy-4'-methanesulfonylaminophenyl)-benzimidazole One and one-half grams (4.0 mmol) of 5-methoxycarbonyl-2-(2'-methoxy-4'-methanesulfonylamino-phenyl)-benzimidazole and 10 ml of methylamine were heated for four hours to 120° C. in a steel canister. Then, excess methylamine was evaporated off, and the residue was dissolved in a small amount of water and neutralized with concentrated hydrochloric acid. After the solution was evaporated, the crude product obtained was purified by chromatography (150 gm of silica gel; eluant: methylene chloride with 10% ethanol).

Yield: 67.0% of theory,
M.p.: 120°–124° C.
$C_{17}H_{18}N_4O_4S$ (374.43)
Calc.: C, 54.53; H, 4.85; N, 14.96; S, 8.56. Found: C, 54.21; H, 4.97; N, 14.87; S, 8.28.

EXAMPLE 92

5-Hydroxymethyl-2-(2'-methoxy-4'-methanesulfonylamino-phenyl)benzimidazole

A quantity of 1.9 gm (5.1 mmol) of 5-methoxycarbonyl-2-(2'-methoxy-4'-methanesulfonylamino-phenyl)-benzimidazole, dissolved in 300 ml of absolute tetrahydrofuran, was added dropwise, under stirring, to a suspension of 700 mg of lithium aluminium hydride in 50 ml of absolute tetrahydrofuran. After the solution was stirred overnight at ambient temperature, 30 ml of water were added, any insoluble components were filtered off, and the filtrate was concentrated to dryness in vacuo. The crude product thus obtained was purified by chromatography over 200 gm of silica gel (eluant: methylene chloride with 3 to 10% of ethanol).

Yield: 83.3% of theory.
$C_{16}H_{17}N_3O_4S$ (347.4)
Calc.: C, 55.32; H, 4.93; N, 12.10; S, 9.23. Found: C, 54.95; H, 5.22; N, 11.79; S, 9.14.

EXAMPLE 93

5-Amino-2-(2'-methoxy-4'-N-methyl-methanesulfonamino-phenyl)-benzimidazole

An amount of 5.8 gm (15.4 mmol) of 5-nitro-2-(2'-methoxy-4'-methylmethanesulfonamino-phenyl)-benzimidazole was suspended in 250 ml of ethanol, 7.5 gm of Raney nickel were added, and 20 ml of hydrazine hydrate were added dropwise, under stirring. Then the mixture was stirred overnight at ambient temperature, the catalyst was removed by suction filtration, the filtrate was concentrated by evaporation, and the residue was recrystallized from ethanol.

Yield: 20.5% of theory,
M.p.: 216°–218° C.
$C_{16}H_{18}N_4O_3S$ (346.42)
Calc.: C, 55.47; H, 5.24; N, 16.17; S, 9.26. Found: C, 55.22; H, 5.38; N, 16.00; S, 9.24.

EXAMPLE 94

5-Amino-2-(2'-methoxy-4'-methanesulfonylaminophenyl)-benzimidazole dihydrochloride Prepared analogously to Example 93 from 5-nitro-2-(2'-methoxy-4'-methanesulfonylamino-phenyl)-benzimidazole with hydrazine hydrate and Raney nickel.

Yield: 68.5% of theory,
M.p.: 215°–217° C.
$C_{15}H_{16}N_4O_3S \times 2HCl$ (405.32)
Calc.: C, 44.45; H, 4.48; N, 13.82; S, 7.91; Cl, 17.50. Found: C, 44.08; H, 4.71; N, 13.92; S, 7.80; Cl, 17.75.

EXAMPLE 95

5-Hydroxy-2-(2'-methoxy-4'-methanesulfonylaminophenyl)-benzimidazole

Quantities of 1.6 gm (10 mmol) of 4-hydroxy-1,2-phenylenediamine and 4.9 gm (20 mmol) of 2-methoxy-4-methansulfonylamino-benzoic acid were refluxed for 1.5 hours, under stirring, in 80 ml of phosphorus oxychloride. The resulting dark solution was then decanted off to eliminate any undissolved components, the phosphorus oxychloride was distilled off in vacuo, and the residue was carefully mixed with 10 gm of crushed ice. Ten milliliters of 4N sodium hydroxide were added to the suspension thus obtained, and the resulting mixture was stirred for one hour at ambient temperature. It was then neutralized with concentrated hydrochloride acid, while being cooled, the solution was evaporated in vacuo to about 3 to 4 ml, the crude product precipitate was subjected to suction filtration, and the resultant crude product was purified by chromatography (250 gm of silica gel, eluant: methylene chloride with 5% ethanol).

Yield: 9.7% of theory,
M.p. decomposition from 150° C.
$C_{15}H_{15}N_3O_4S$ (333.38)
Calc.: C, 54.04; H, 4.53; N, 12.60; S, 9.62. Found: C, 54.36; H, 4.91; N, 12.31; S, 9.77.

EXAMPLE 96

5-Aminocarbonyl-2-(2'-methoxy-4'-methanesulfonyloxy-phenyl)-benzimidazole

One gram (2.91 mmol) of 5-cyano-2-(2'-methoxy-4'-methanesulfonyloxy-phenyl)-benzimidazole was added batchwise to 15 ml of concentrated sulfuric acid, and the resulting mixture was stirred for 24 hours at ambient temperature. The solution was then poured onto 300 ml of ice water, and the product precipitated was subjected to suction filtration and recrystallized from methanol.
Yield: 830 mg (78.9% of theory),
M.p. sinters from 185° C.

EXAMPLE 97

2-(2'-Methoxy-4-methanesulfonylamino-phenyl)-6-hydroxy-imidazo[4,5-b]pyridine

Prepared analogously to Example 14 from 2,3-diamino-5-acetoxypyridine and 2-methoxy-6-methanesulfonylamino-benzoic acid. The product was purified over a silica gel column [eluant: first methylene chloride, then methylene chloride/ethanol (50:1 to 9:1)].
Yield: 0.06 gm (69% of theory),
M.p. 225° C. (decomposition).
Mass spectrum: molar mass 334.

EXAMPLE 98

2-(2'-Methoxy-4'-methylthiomethyl-phenyl)-imidazo[4,5-c]pyridine

Prepared analogously to Example 14 from 3,4-diaminopyridine and 2-methoxy-4-methylthiomethyl-benzoic acid.
Yield: 15.8% of theory,
$C_{15}H_{15}N_3OS$ (285.35)
Calc.: C, 63.13; H, 5.30; N, 14.73. Found: C, 62.91; H, 4.99; N, 14.48.
$^1$H—NMR spectrum (DMSO-$d_6$/CD$_3$OD): $\delta$=2.1 (s, 3H); 3.7 (s, 2H); 4.1 (s, 3H); 6.9–7.3 (m, 2H); 8.0–8.7 (m, 3H); 9.25–9.35 (broad s, 1H) ppm.

EXAMPLE 99

2-(2'-Methoxy-4'-methylsulfinylmethyl-phenyl)-imidazo[4,5-c]pyridine

Prepared analogously to Example 33 from 2-(2'-methoxy-4'-methyl-thiomethyl-phenyl)-imidazo[4,5-c]pyridine and peracetic acid.
Yield: 16.8% of theory,
$^1$H—NMR spectrum (DMSO-$d_6$/CD$_3$OD): $\delta$=2.6 (s, 3H); 4.1 (s, 5H); 6.9–7.3 (m, 2H); 8.0–8.7 (m, 3H); 9.3–9.4 (broad s, 1H) ppm.

EXAMPLE 100

2-(2'-Methoxy-4'-methylsulfonylmethyl-phenyl)-imidazo[4,5-c]pyridine

Prepared analogously to Examole 31 from 2-(2'-methoxy-4'-methyl-thiomethyl-phenyl)-imidazo[4,5-c]pyridine and peracetic acid.
Yield: 38.5% of theory.
$C_{15}H_{15}N_3O_3S$ (317.38)
Calc.: C, 56.77; H, 4.76; N, 13.24. Found: C, 56.41; H, 4.51 N, 12.78.
$^1$H—NMR spectrum (DMSO-$d_6$/CD$_3$OD): $\delta$=2.9 (s, 3H); 4.1 (s, 3H); 4.4 (s, 2H); 7.0–7.4 (m, 2H); 8.0–8.6 (m, 3H); 9.2–9.3 (broad s, 1H) ppm.

EXAMPLE 101

2-(2'-Methoxy-4'-N-methyl-trifluoromethanesulfonylamino-phenyl)-imidazo[4,5-b]pyridine Prepared analogously to Example 14 from 2,3-diaminopyridine and 2-methoxy-4-N-methyl-trifluoromethanesulfonylamino-benzoic acid.
Yield: 12.1% of theory,
M.p. >250° C.
$C_{15}H_{13}F_3N_4O_3S$ (386.35)
Calc.: C, 46.63; H, 3.39; N, 14.50. Found: C, 46.93; H, 3.48; N, 14.11.

EXAMPLE 102

2-(2'-Methoxy-4'-N-ethyl-trifluoromethanesulfonylamino-phenyl)-benzimidazole hydrochloride Prepared analogously to Example 14 from o-phenylenediamine and 2-methoxy-4-N-ethyl-trifluoromethanesulfonylamino-benzoic acid.
Yield: 24.7% of theory.
$C_{13}H_{17}ClF_3N_3O_3S$ (435.85)
Calc.: C, 46.84; H, 3.93; N, 9.64. Found: C, 47.12; H, 4.01; N, 9.33.

EXAMPLE 103

2-(2'-Methoxy-4'-trifluoromethanesulfonylamino-phenyl)-benzimidazole hydrochloride Prepared analogously to Example 14 from o-phenylenediamine and 2-methoxy-4-trifluoromethansulfonylamino-benzoic acid.
Yield: 18.3% of theory,
M.p.: >220° C.
$C_{15}H_{13}ClF_3N_3O_3S$ (407.8)
Calc.: C, 44.18; H, 3.21; N, 10.31. Found: C, 44.33; H, 3.17; N, 10.11.

EXAMPLE 104

2-(2'-Methoxy-4'-trifluoromethanesulfonylamino-phenyl)-imidazo[4,5-b]pyridine hydrochloride Prepared analogously to Example 14 from 2,3-diaminopyridine and 2-methoxy-4-trifluoromethanesulfonylamion-benzoic acid.
Yield: 15.1% of theory,
M.p.: >220° C.
$C_{14}H_{12}ClF_3N_4O_3S$ (408.0)
Calc.: C, 41.13; H, 2.96; N, 13.71. Found: C, 40.88; H, 2.79; N, 13.52.

The following examples illustrate a few pharmaceutical compositions comprising a compound of the present invention as an active ingredient and represent the best modes contemplated of using the invention. The compounds 8-(2'-methoxy-4'-methanesulfonyloxy-phenyl)-purine and 8-(2'-methoxy-4'-methanesulfonyloxyphenyl)-imidazo[4,5-b]pyridine are designated Active Ingredient A and Active Ingredient B, respectively. It should be understood that one or more other compounds of Formula I, or a non-toxic, pharmacologically acceptable acid addition salt thereof, can be used in place of Active Ingredient A or B.

EXAMPLE 105

Tablets Containing 100 mg of Active Ingredient A

Each tablet has the following composition:

| Component | Amount (mg) |
| --- | --- |
| Active Substance A | 100.0 |
| Lactose | 50.0 |
| Polyvinylpyrrolidone | 5.0 |
| Carboxymethyl cellulose | 19.0 |
| Magnesium stearate | 1.0 |
| TOTAL: | 175.0 |

Preparation:
The active Ingredient A and lactose are homogeneously moistened with an aqueous solution of polyvinylpyrrolidone, passed through a screen with a mesh size of 1.5 mm, dried in a circulating air drier at 50° C., and then passed through a 1 mm mesh screen. The granulate is combined with the remaining excipients, and the final mixture is compressed to form tablets.
Weight of tablet: 175 mg
Punch: 8 mm

EXAMPLE 106

Coated Tablets Containing 50 mg of Active Ingredient A

Each tablet core has the following composition:

| Component | Amount (mg) |
|---|---|
| Active Subtance A | 50.0 |
| Dried corn starch | 20.0 |
| Soluble starch | 2.0 |
| Carboxylmethyl cellulose | 7.0 |
| Magnesium stearate | 1.0 |
| TOTAL: | 80.0 |

Preparation:

The Active Ingredient A and corn starch are uniformly moistened with an aqueous solution of the soluble starch, passed through a screen with a mesh size of 1.0 mm, dried in a circulating air drier at 50° C., and then passed through a 1.0 mm mesh screen. The granulate and remaining excipients are combined and compressed to form tablet cores.
Weight of core: 80 mg
Punch: 6 mm
Radius of curvature: 5 mm The finished cores are coated in the usual manner with a sugar coating by using a coating pan.
Weight of coated tablet: 120 mg

EXAMPLE 107

Suppositories Containing 75 mg of Active Ingredient A

Each suppository has the following composition:

| Component | Amount (mg) |
|---|---|
| Active Ingredient A | 75.0 |
| Suppository mass (e.g., WITEPSOL ® H19 or W45, available from Chemische Werke Witten GmbH) | 1625.0 |
| TOTAL: | 1700.0 |

Preparation:

The suppository mass is melted, and after the molten mass has been cooled to 38° C., ground Active Ingredient A is homogeneously dispersed therein. The molten mass is then cooled to 35° C. and poured into slightly chilled suppository molds.
Weight of one suppository: 1.7 gm.

EXAMPLE 108

Ampules Containing 50 mg of Active Ingredient B

Each ampule has the following composition:

| Component | Amount |
|---|---|
| Active Ingredient B | 50.0 mg |
| Sorbitol | 250.0 mg |
| Distilled water q.s. ad | 5.0 ml |

Preparation:

The Active Ingredient B and sorbitol are dissolved in distilled water, then the solution is made up to the volume given and filtered under sterile conditions.
Bottling: in 5 ml ampules
Sterilization: 20 minutes at 120° C.

EXAMPLE 109

Suspension Containing 2.50 mg/ml of Active Ingredient B

One hundred milliliters of suspension has the following composition:

| Component | Amount |
|---|---|
| Active Ingredient B | 5.0 gm |
| Methyl p-oxybenzoate | 0.035 gm |
| Propyl p-oxybenzoate | 0.015 gm |
| Anisole | 0.05 gm |
| Methanol | 0.06 gm |
| Sodium saccharin | 1.0 gm |
| Glycerol | 10.0 gm |
| Ethanol | 40.0 gm |
| Distilled water q.s. ad | 100.0 ml |

Preparation:

The benzoates are dissolved in ethanol, and then the anisole and methanol are added. Subsequently, the active substance, glycerol, and sodium saccharin, dissolved in water, are added thereto. The solution is then filtered until clear.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A compound of the formula

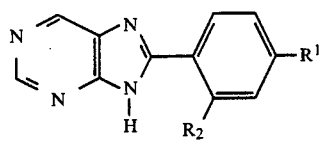

wherein
R$_1$ is (alkane of 1 to 3 carbon atoms)sulfonylamino, N-(alkyl of 1 to 3 carbon atoms)-(alkane of 1 to 3 carbon atoms)sulfonylamino, aminocarbonyl, (alkyl of 1 to 3 carbon atoms)amino-carbonyl, di(alkyl of 1 to 3 carbon atoms)amino-carbonyl, aminosulfonyl, (alkyl of 1 to 3 carbon atoms)aminosulfonyl, or di(alkyl of 1 to 3 carbon atoms)amino-sulfonyl; and
R$_2$ is alkoxy of 1 to 3 carbon atoms;
a tautomer thereof; or a non-toxic, pharmacologically acceptable acid addition salt thereof.

2. A compound of claim 1, where
R$_1$ is methanesulfonylamino, N-methyl-methanesulfonylamino, aminocarbonyl, aminosulfonyl, methylaminosulfonyl or dimethylaminosulfonyl; and
R$_2$ is methoxy;
a tautomer thereof; or a non-toxic, pharmacologically acceptable acid addition salt thereof.

3. A compound of claim 2, which is 8-(2'-methoxy-4'-aminocarbonyl-phenyl)-purine, a tautomer thereof, or a non-toxic pharmaceutical acceptable acid addition salt thereof.

4. A compound of claim 2, which is 8-[2'-methoxy-4'-(N-methyl-methanesulfonylamino)-phenyl]-purine, a tautomer thereof, or a non-toxic pharmacologically acceptable acid addition salt thereof.

5. A compound of claim 2, which is 8-(2'-methoxy-4'-methylaminosulfonyl-phenyl)-purine, a tautomer thereof, or a non-toxic pharmacologically acceptable acid addition salt thereof.

6. A cardiotonic pharmaceutical composition consisting essentially of an inert pharmaceutical carrier and an effective cardiotonic amount of a compound of claim 1.

7. The method of treating a cardiac insufficiency in a warm-blooded animal in need thereof which comprises perorally, parenterally or rectally administering to said animal an effective cardiotonic amount of a compound of claim 1.

* * * * *

UNITED STATES PATENT AND TRADEMARK OFFICE
CERTIFICATE OF CORRECTION

PATENT NO.  :  4,696,931

DATED       :  September 29, 1987

INVENTOR(S) :  NORBERT HAUEL ET AL.

It is certified that error appears in the above-identified patent and that said Letters Patent is hereby corrected as shown below:

Column 1, line 9:   "pharmacologinal" should read
                    -- pharmacological --.

Column 2, line 57:  "methylamioncarbonyl" should read
                    -- methylaminocarbonyl --.

Column 12, line 43: "3.6 mg" should read -- 3.6 gm --.

Column 21, line 54: "2-(2'-carboxy-phenyl)' should read
                    -- 2-(2'-methoxy-4'-carboxy-phenyl) --

Column 24, line 45: "or" should read -- of --.

Column 35, line 49: "Examole" should read -- Example --.

Column 36, line 36: "(408.0)" should read -- (408.8) --.

Signed and Sealed this

Twenty-sixth Day of April, 1988

Attest:

DONALD J. QUIGG

Attesting Officer   Commissioner of Patents and Trademarks